United States Patent
Nebolsin et al.

(10) Patent No.: US 11,845,740 B2
(45) Date of Patent: Dec. 19, 2023

(54) GLUTAMINYL CYCLASE INHIBITORS AND THE USE THEREOF IN TREATMENT OF VARIOUS DISEASES

(71) Applicant: OBSCHESTVO S OGRANICHENNOI OTVETSTVENNOSTIYU "PHARMENTERPRISES", Moscow (RU)

(72) Inventors: Vladimir Evgenievich Nebolsin, Der. Borzye (RU); Anastasia Vladimirovna Rydlovskaya, St. Petersburg (RU); Tatyana Alexandrovna Kromova, Khimki (RU)

(73) Assignees: LTD "VALENTA-INTELLEKT", Moscow (RU); Vladimir Evgenievich Nebolsin, Moscow (RU)

( * ) Notice: Subject to any disclaimer, the term of this patent is extended or adjusted under 35 U.S.C. 154(b) by 0 days.

(21) Appl. No.: 16/472,172

(22) PCT Filed: May 24, 2018

(86) PCT No.: PCT/RU2018/050058
§ 371 (c)(1),
(2) Date: Jun. 20, 2019

(87) PCT Pub. No.: WO2018/217139
PCT Pub. Date: Nov. 29, 2018

(65) Prior Publication Data
US 2020/0087285 A1 Mar. 19, 2020

(30) Foreign Application Priority Data

May 26, 2017 (RU) .................... 2017118350
Oct. 27, 2017 (RU) .................... 2017137615

(51) Int. Cl.
| | | |
|---|---|---|
| C07D 403/12 | (2006.01) | |
| A61P 25/02 | (2006.01) | |
| A61P 37/00 | (2006.01) | |
| A61P 1/00 | (2006.01) | |
| A61P 29/00 | (2006.01) | |
| A61K 31/4178 | (2006.01) | |
| A61P 11/00 | (2006.01) | |
| A61P 13/12 | (2006.01) | |
| A61P 17/06 | (2006.01) | |

(Continued)

(52) U.S. Cl.
CPC ............ *C07D 403/12* (2013.01); *A61P 25/02* (2018.01); *A61P 37/00* (2018.01); *C12N 9/104* (2013.01); *C12Y 203/02005* (2013.01)

(58) Field of Classification Search
CPC ........ C07D 403/12; A61P 25/02; A61P 37/00; C12Y 203/02005; A61K 31/4178; C12N 9/104; C12N 9/10
See application file for complete search history.

(56) References Cited

U.S. PATENT DOCUMENTS

| | | | |
|---|---|---|---|
| 10,392,604 B2 * | 8/2019 | Egorov | .................. A61P 31/16 |
| 2009/0068699 A1 | 3/2009 | Schilling et al. | |
| 2016/0031858 A1 * | 2/2016 | Nebolsin | ................. A61P 25/28 |
| | | | 514/367 |

FOREIGN PATENT DOCUMENTS

| | | |
|---|---|---|
| CN | 105358548 A | 2/2016 |
| GB | 2447017 A | 9/2008 |

(Continued)

OTHER PUBLICATIONS

Asthma-Prevention, 2020, https://www.medicalnewstoday.com/articles/324517.*
Obesity-Prevention, 2020, https://www.cdc.gov/obesity/strategies/index.html.*
RheumatoidArthritis-Prevention, 2020, https://www.healthline.com/health/rheumatoid-arthritis-prevention.*
Asthma-Cure, 2020, https://www.healthline.com/health/asthma/is-asthma-curable.*
RheumatoidArthritis-Cure, 2020, https://www.mayoclinic.org/diseases-conditions/rheumatoid-arthritis/diagnosis-treatment/drc-20353653.*

(Continued)

*Primary Examiner* — Sun Jae Yoo
(74) *Attorney, Agent, or Firm* — BCF LLP

(57) ABSTRACT

The invention relates to chemistry of organic substances, pharmacology and medicine, and concerns treating diseases associated and with aberrant activity of cells of the immune system, more particularly for treating lung, respiratory tract and abdominal diseases, radiation sickness and pain syndrome, and also other diseases by using compounds of formula (A)

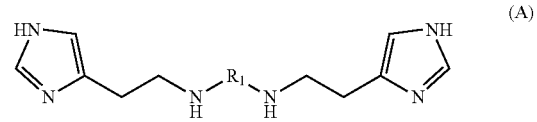

wherein
R$_1$ is —C(O)—R$_2$—(O)— or —R$_2$—C(O)— group, where R$_2$ is —(CH$_2$)$_n$-group optionally substituted with one or two C$_1$-C$_6$ alkyls, or phenyl,
n is an integer from 0 to 4;
wherein compounds are selected from the group consisting of the group of compounds as set out in the description. These compounds, as well as pharmaceutically acceptable salts thereof, are highly effective in inhibiting glutaminyl cyclase, which is involved, in particular, in processes of post-translational modification of chemokines and chemotaxis of monocytes, macrophages and other cells of the immune system. This invention also relates to pharmaceutical compositions comprising a therapeutically effective amount of the compounds of formula (A) as defined above.

5 Claims, 1 Drawing Sheet

(51) Int. Cl.
    *A61K 47/00*     (2006.01)
    *A61K 45/06*     (2006.01)
    *A61P 3/04*     (2006.01)
    *A61P 11/06*     (2006.01)
    *A61P 17/00*     (2006.01)
    *C12N 9/10*     (2006.01)

(56) References Cited

FOREIGN PATENT DOCUMENTS

| | | |
|---|---|---|
| RU | 2015120055 A | 12/2016 |
| WO | 2014168523 A4 | 1/2015 |
| WO | 2016190785 A1 | 12/2016 |

OTHER PUBLICATIONS

Brauer et al., JCI, 2016, 126(4), 1245-1247.*
Bronchitis, 2022, https://www.americanriverurgentcare.com/blog/the-flu-vs-bronchitis-how-to-tell-the-difference#:~:text=Given%20that%20bronchitis%20is%20a,what%20you%20think%20you%20have.*
COPD, 2022, https://www.pulmonologyadvisor.com/home/resources/lungs-bugs/influenza-in-chronic-obstructive-pulmonary-disease-complications-and-management/.*
Emphysema, 2022.*
Rhinitis, 2022, http://www.emro.who.int/health-topics/influenza/influenza-seasonal.html#:~:text=Seasonal%20influenza%20is%20a%20viral,cough%2C%20sore%20throat%20and%20rhinitis.*
Rhinosinusitis, 2022, https://www.cedars-sinai.org/health-library/diseases-and-conditions/a/acute-bacterial-rhinosinusitis-1.html.*
Pharyngitis, 2022, https://www.gohealthuc.com/library/sore-throat-first-flu-symptom.*
International Search Report dated Oct. 4, 2018, for PCT Patent Application No. PCT/RU2018/050058 filed on May 24, 2018, 3 pages.
What You Should Know About Flu Antiviral Drugs, 2022, https://www.cdc.gov/flu/treatment/whatyoushould.htm.
Podyminogin et al., "Synthetic RNA-cleaving molecules mimicking ribonuclease A active center. Design and cleavage of tRNA transcripts", Nucleic Acids Research, vol. 21, No. 25, pp. 5950-5956, Published on Nov. 16, 1993, DOI: 10.1093/nar/21.25.5950.
Russian Search Report dated Nov. 1, 2022 issued in respect of the related Russian Patent Application No. RU 2018129098.
Search Report dated Apr. 8, 2023 in respect of the counterpart Chinese patent application 201880005216.3.

* cited by examiner

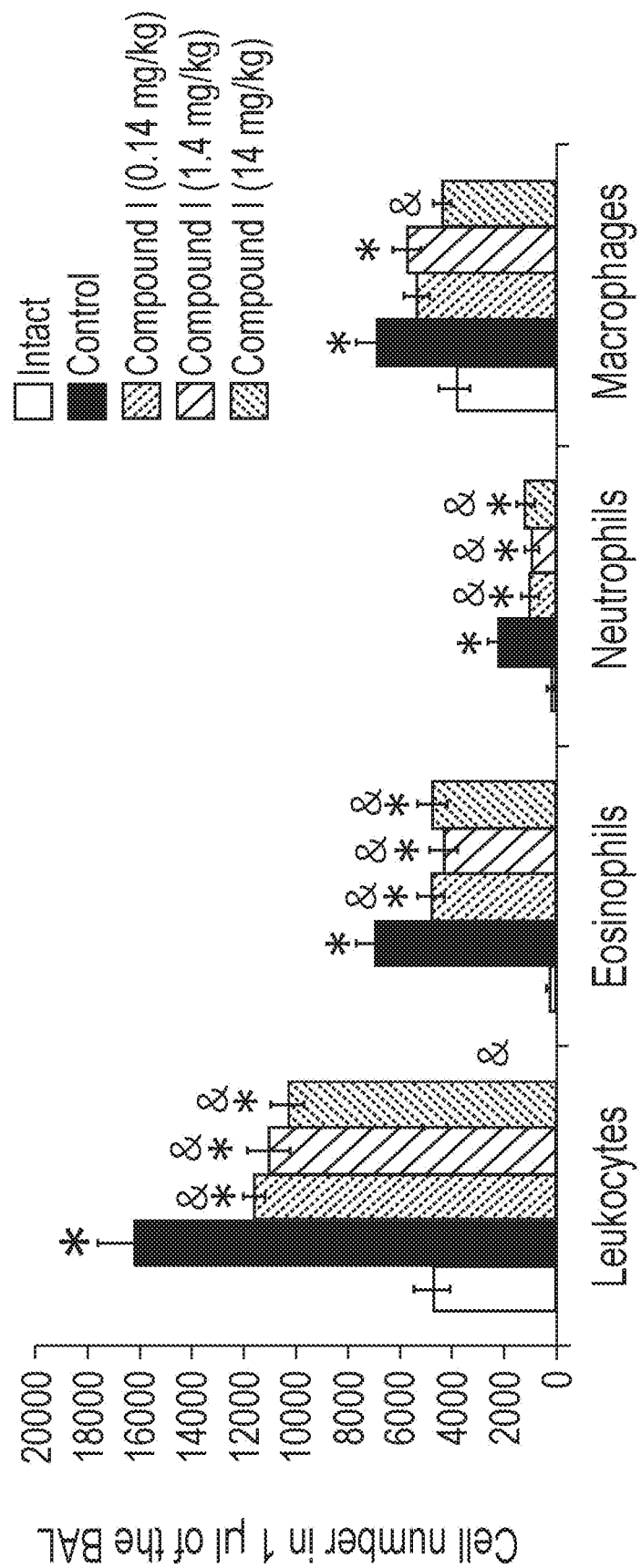

GLUTAMINYL CYCLASE INHIBITORS AND THE USE THEREOF IN TREATMENT OF VARIOUS DISEASES

CROSS REFERENCE TO RELATED APPLICATIONS

This application is a national stage application under 35 U.S.C. § 371 of International Application No. PCT/RU2018/050058, filed internationally on May 24, 2018, which claims priority of Russian Application No. 2017118350 filed on May 26, 2017, and Russian Application No. 2017137615 filed on October 10, 2017.

FIELD OF THE ART

The invention relates to chemistry of organic compounds, pharmacology and medicine, and concerns treating diseases associated with aberrant activity of cells of the immune system, in particular for treating lung, respiratory tract and abdominal disease. The present invention also concerns the treatment of radiation sickness and pain syndrome, and also other diseases by using compounds which are effective in inhibiting an enzyme-glutaminyl cyclase, involved in particular in post-translation modification of chemokines and chemotaxis of cells of the immune system.

BACKGROUND OF THE INVENTION

Chemotaxis or directed movement of cells of the immune system following the concentration gradient of some endogenous and exogenous substances (chemoattractants) is one of the major constituents of functioning cells of the immune system. The excessive influx of cells of the immune system usually causes the excessive activity of cells of the immune system and injury of surrounding organs and tissue. The understanding of participants and processes associated with the chemotaxis process, at the molecular level, could result in novel effective approaches in the treatment and prevention of a number of diseases associated with aberrant activity of cells of the immune system.

Chemokines of the CCL family (CCL2, CCL7, CCL8, CCL13), which are ligands of the CCR2 receptor, are the most potent factors of chemotaxis of monocytes and macrophages in mammals (Biochem J. 2012 Mar. 1; 442(2): 403-12). Chemokines of the CCL family are the important class of cytokines required for the activation of neutrophils and monocytes, and attract the involvement of these cells into the site of inflammatory. However, high concentrations of chemokines as a rule cause the excessive influx of cells of the immune system. Aberrant activity of cells of the immune system may result in serious injuries of surrounding organs and tissue. For example, in some cases, lipid oxidation products may activate vascular endothelial cells (intima), which results in the isolation of CCL2, the involvement of macrophages which in turn secrete inflammatory markers, provoking the injury of the arterial wall and the development of atherosclerosis (Mol Cell. 1998 August; 2(2):275-81; Nature. 1998 Aug. 27; 394(6696):894-7). Analogous pathogenetic picture may be observed in case of radiation-induced injury of respiratory tract tissues: the injury and activation of epithelium cells of lings and respiratory tracts results in the isolation of CCL2, which in turn causes the extravasation of immune cells and circulating tumor cells into lings and respiratory tract (Antioxid Redox Signal. 2018 Apr. 2. doi: 10.1089/ars.2017.7458).

Role of chemokines of the CCL family in pathophysiology of a number of autoimmune and allergic conditions mediated by aberrant activity of CCR2+, CD4+ and CD1610 monocytes (rheumatoid arthritis, multiple sclerosis) is known. Furthermore, the chemokines of the CCL family (in particular CCL2) are involved in the pathogenesis of the obesity, metabolic syndrome, chronic pain, fibrosis, non-alcohol fatty liver disease and some forms of cancer.

The suppression of aberrant activity of cells of the immune system by inhibiting the CCL-mediated chemotaxis could be in great demand for the treatment of a range of diseases such as acute lung injury, bronchial asthma, bronchitis, chronic obstructive pulmonary disease, Crohn's disease, diabetic nephropathy and the like. For example, in case of diabetic nephropathy, the influence of glucose in high concentrations results in the increase in CCL2 secretion by renal tubular cells, which in turn causes the migration of monocytes (Kidney Int. 2006 January; 69(1):73-80). The increase in the concentration of monocytes in renal tissues and their maturation to macrophages causes the development of aberrant response associated with the isolation of the greater quantity of chemokines and active oxygen forms which injuring the surrounding renal cells (Mediators Inflamm. 2012; 2012:146154). The injury of renal tissue results in the development and maintenance of aberrant activity of cells of the immune system and the further destruction of renal tissues, and the blockade of the interaction of CCL2/CCR2 by low-molecular antagonists reduces the intensity of pathology (Nephrol Dial Transplant. 2013 July; 28(7):1700-10). Analogous processes are characteristic for the pathogenesis of non-alcoholic fatty liver disease: the accumulation of fatty acids in liver cells results in the activation of a NF-кB signal pathway and the development of inflammatory reaction inducing the release of anti-inflammatory cytokines such as IL-6 and CCL2. The release of anti-inflammatory cytokines results in the migration of monocytes to the site of inflammation and the development of aberrant response associated with the isolation of a greater quantity of chemokines and active oxygen forms injuring surrounding cells (Int J Exp Pathol. 2013 June; 94(3): 217-225).

Members of the CCL family (CCL2, CCL7, CCL8, CCL13), fractalkine, as well as of a range of other hormones and secreted proteins contain a pyroglutamic acid residue (pE), whose role is to protect against the degradation by aminopeptidases (Chem Immunol. 1999; 72:42-56; Biochemistry. 1999 Oct. 5; 38(40):13013-25). The the pyroglutamation of the N-terminal residue is catalyzed by enzymes-glutaminyl cyclase (QPCT or QC) (J Biol Chem. 2003 Dec. 12; 278(50):49773-9; J Mol Biol. 2008 Jun. 20; 379(5):966-80). Glutaminyl cyclase has a wide substrate specificity and participates in the post-translational modification of a range of peptide molecules. It has been shown in the studies of the substrate specificity of glutaminyl cyclase that the enzyme may catalyze the pyroglutamation of different substrates regardless of the polypeptide chain length (FEBS Lett. 2004 Apr. 9; 563(1-3):191-6, J Biol Chem. 2011 Apr. 8; 286(14): 12439-49).

It has been shown in experimental studies that the inhibition of glutaminyl cyclases results in a drastic reduction in chemoattractant activity of non-pyroglutamated forms of CCL2, CCL7, CCL8 and CCL13 chemokines (Biochem. J. (2012) 442, 403-412) and fractalkine (Biosci Rep. 2017 Aug. 23; 37(4)). Thus, it is obvious that glutaminyl cyclase inhibitors may be used for the therapy of a wide range of diseases, and in particular, lung and respiratory tract diseases, such as bronchial asthma, acute and chronic bronchitis, pharyngitis, pulmonary emphysema, rhinitis, rhinosinusitis and chronic obstructive lung disease. The pathogenesis of the diseases is associated with the excessive cytokine production and in particular monocyte chemoattractant proteins CCL2 and CCL7 (Am J Respir Cell Mol Biol. 2014 January; 50(1):144-57) and fractalkine (Expert Opin Ther Targets. 2010 February; 14(2):207-19), which are glutaminyl cyclase substrates (Biosci Rep. 2017 Aug. 23; 37(4). pii: BSR20170712; EMBO Mol Med. 2011 September; 3(9): 545-58). It has been shown that the neutralization of CCL2 and CCL7 with the use of antibodies considerably reduces the influx of leukocytes, monocytes and neutrophils to respiratory tract of experimental animals (Am J Respir Cell Mol Biol. 2014 January; 50(1):144-57). The impact of bacterial lipopolysaccharides, lipoteichoic acid or other irritants to the mucosa of the respiratory organs system results in the increase in CCL2 secretion by bronchial smooth muscle cells (Am J Physiol Lung Cell Mol Physiol. 2012 Apr. 15; 302(8):L785-92) and the growth of CCL2 concentration in bronchoalveolar lavage (Mol Immunol. 2011 July; 48(12-13):1468-76). The increase in the CCL2 concentration in turn causes the migration of eosinophils, monocytes and basophils and the development of aberrant response associated with the isolation of a greater quantity of chemokines (TNFα, IL-1, IL-6, IL-4) and active oxygen forms which injury surrounding cells of bronchi and respiratory organs (Immunobiology. 2016 February; 221(2):182-7; Int J Biol Sci. 2012; 8(9):1281-90; Mol Immunol. 2013 November; 56(1-2):57-63). The injury of bronchi results in the development and maintenance of the aberrant activity of cells of the immune system and the further destruction of respiratory organ tissues. According to in vivo models of allergic asthma, the blockade of interaction CCL2/CCR2 by low-molecular antagonists has shown the significant efficacy (Int Arch Allergy Immunol. 2015; 166(1):52-62).

It is important to note that the CCL2-mediated development of neutrophil inflammation and the development of the aberrant response related to the release of pyrogenic cytokines (IL-1, TNFα, IL-6) results in the increase in temperature and development of fever (J Infect Dis. 1999 March; 179 Suppl 2:S294-304; Front Biosci. 2004 May 1; 9:1433-49.).

In addition to fever and elevated temperature, pain syndrome is also the extremely common symptom of various diseases. It is obvious that the reduction of the intensity of the aberrant response related to the release of the increased number of active forms of oxygen which damage surrounding tissues should in itself result in the decrease in the intensity of the pain syndrome. However, in recent work, the key role of fractalkine in the pathogenesis of chronic pain has been shown (J Neurochem. 2017 May; 141(4):520-531).

Glutaminyl cyclase inhibitors can be used for the therapy of various autoimmune diseases, in particular rheumatoid arthritis and psoriasis. Fractalkine is one of the key proinflammatory mediators involved in the development of autoimmune diseases. The interaction between fractalkine and its unique receptor (CX3CR1) induces the cell adhesion, chemotaxis and cell survival (Mol Interv. 2010 October; 10(5):263-70). The fractalkine level is increased in patients with rheumatoid arthritis (PA) (Mod Rheumatol. 2017 May; 27(3):392-397) and psoriasis (Ann Clin Lab Sci. 2015 Fall; 45(5):556-61) and correlates with the activity of disease. Fractalkine is expressed on fibroblast-like synoviocytes and endothelial cells in synovial tissue of patients with rheumatoid arthritis. In case of psoriasis, high levels of fractalkine production are observed in dermal papillae and antigen-presenting cells (Br J Dermatol. 2001 June; 144(6):1105-13). The expression of fractalkine is enhanced by the tumor-α necrosis factor and interferon-γ, and in case of rheumatoid arthritis promotes the migration of monocytes, T-cells and osteoclast precursors to the synovial tissue (Mod Rheumatol. 2017 May; 27(3):392-397). The increased expression of fractalkine in dermal papillae likely explains the migration and accumulation of T-cells at these sites in case of psoriasis (Br J Dermatol. 2001 June; 144(6):1105-13). Fractalkine also induces the formation of inflammatory mediators by macrophages, T-cells and fibroblast-like synoviocytes. Moreover, fractalkine promotes angiogenesis and osteoclastogenesis. In the model of collagen-induced arthritis, the use of anti-fractalkine antibodies has allowed to considerably alleviate the pathology process (Mod Rheumatol. 2017 May; 27(3):392-397).

On the basis of the results of recent research studies, it is possible to assert that the inhibition of the CCL-mediated chemotaxis is the new perspective therapeutic approach to the treatment of radiation sickness (Antioxid Redox Signal. 2018 Apr. 2. doi: 10.1089/ars.2017.7458, Int J Radiat Biol. 2015 June; 91(6):510-8). It has been shown in animal models that the intensity of radiation-induced dysfunction of vessels may be efficiently reduced due to the inhibition of the CCL-mediated signal pathways. The use of knockout animals for the CCL2 receptor gene as well as in case of use of antagonists of said receptor blocks the radiation-induced alteration in morphology and the destruction of endothelial cells, and prevents from the development of respiratory tract inflammation directly after the radiation (Antioxid Redox Signal. 2018 Apr. 2. doi: 10.1089/ars.2017.7458). Moreover, the suppression of CCL-mediated signal pathways allows to significantly reduce the intensity of radiation-induced pulmonary fibrosis that is one of the main "deferred" side effects of the radiation.

Thus, based on the literature data, it is possible to conclude that the strategy directed to the inhibition of glutaminyl cyclase is the possible approach to the treatment of autoimmune diseases, obesity, diseases of lung, respiratory tract and abdominal cavity, radiation sickness and pain syndrome.

There are currently known glutaminyl cyclase inhibitors comprising sulfolipids (WO 2017/046256), derivatives of flavonoids (Bioorg Med Chem. 2016 May 15; 24(10):2280-6), pyridine derivatives (US 2015/0291632) and some small molecule described in recent works (J Med Chem. 2017 Mar. 23; 60(6):2573-2590; WO 2014/193974, US 2015/0291557). The closest analogues of the compound that is the object of the present invention are shown in publications of Probiodrug Aktiengesellschaft (J Biol Chem. 2003 Dec. 12; 278(50):49773-9). This work describes glutaminyl cyclase inhibitors based on imidazole derivatives. However, in structures of compounds published by the company Probiodrug Aktiengesellschaft imidazole comprises an aliphatic substituent by one of nitrogen atoms of the imidazole cycle. The introduction of the aliphatic substituent reduces the metabolic stability of the compounds. Furthermore, the introduction of the aliphatic substituent increases the hydrophobicity of the compounds and facilitates the penetration of the compound through the blood-brain barrier, which is clearly unnecessary to suppress the aberrant activity of cells of the immune system and can potentially cause side effects.

So far there is no drug acting as the glutaminyl cyclase inhibitor, which would be used in the therapy of diseases related to the aberrant activity of cells of the immune system, therefore there remains a need for the development and the practical application of new effective drugs based on glutaminyl cyclase inhibitors.

The present invention relates to the use of chemical compounds which are effective in suppressing glutaminyl cyclase in treating respiratory tract and abdominal cavity diseases, radiation sickness and various kinds of pain syndrome, and also other diseases associated with the aberrant activity of cells of the immune system.

BRIEF DESCRIPTION OF THE DRAWINGS

FIG. 1—The influx of inflammatory cells in the broncho-alveolar space in studying specific pharmacological activity of Compound 1 on acute asthma model in guinea pigs (M±m, n=10).

SUMMARY OF THE INVENTION

It is an object of the present invention to provide novel medicaments which are glutaminyl cyclase inhibitors and are effective for treating diseases associated with aberrant activity of cells of the immune system, especially lung, respiratory tract and abdominal diseases, radiation sickness and pain syndrome, and also other iseases associated with aberrant activity of cells of the immune system.

The technical result of the invention is the development and obtainment of effective glutaminyl cyclase inhibitors characterized by high inhibitory activity that allow to use these inhibitors for treating diseases related to the aberrant activity of cells of the immune system, in particular lung and respiratory tract diseases, such as bronchial asthma, acute and chronic bronchitis, pharyngitis, rhinitis (particularly, allergic rhinitis), rhinosinusitis, chronic obstructive pulmonary disease and its manifestations (particularly pulmonary emphysema, bronchial obstruction); diseases of abdominal organs such as Crohn's disease, ulcerative colitis, peritonitises and nephropathy (particularly diabetic nephropathy); radiation sickness and pain syndrome, and also other diseases associated with aberrant activity of cells of the immune system, in particular with the aberrant chemotaxis of cells of the immune.

The indicated aid technical result is achieved by applying compounds of formula (A)

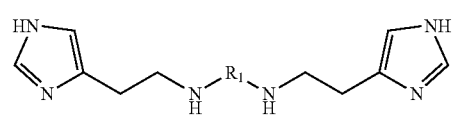

(A)

wherein
$R_1$ is a —C(O)—$R_2$—C(O)— or —$R_2$—C(O)— group, where $R_2$ is a —$(CH_2)_n$— group optionally substituted with one or more $C_1$-$C_6$ alkyls, or phenyl,
n is an integer from 0 to 4;
wherein the indicated compounds of formula (A) are selected from the group consisting of any of compounds I-X, and combinations thereof

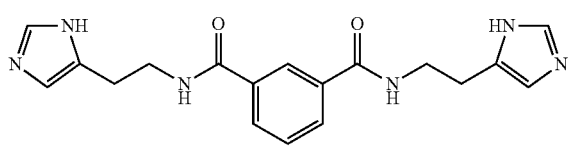

I

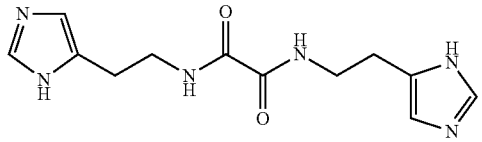

II

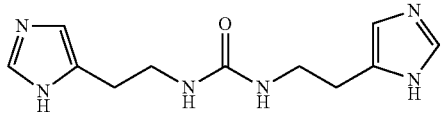

III

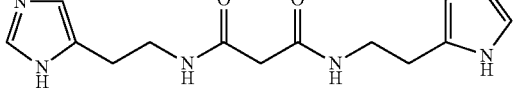

IV

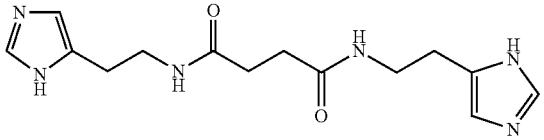

V

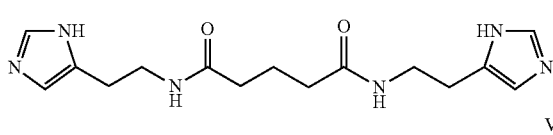

VI

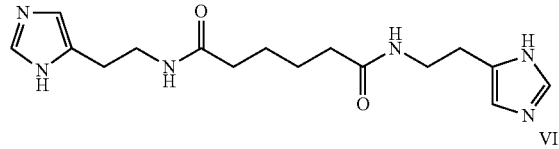

VII

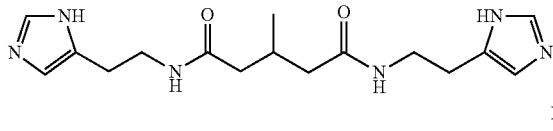

VIII

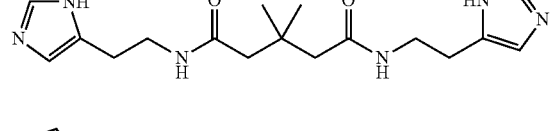

IX

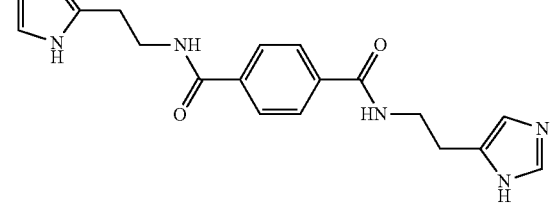

X or pharmaceutically acceptable salts, hydrates, solvates thereof, as glutaminyl cyclase inhibitors.

The indicated technical result is also achieved by the use of the compounds of formula (A) selected from any of compounds I-X or pharmaceutically acceptable salts, hydrates, solvates thereof for producing a pharmaceutical composition for preventing and/or treating a disorder associated with the glutaminyl cyclase activity.

The indicated technical result is also achieved by the use of any one of compounds I-X or salts, hydrates, solvates thereof for producing a pharmaceutical composition for preventing and/or treating a disorder associated with aberrant activity of cells of the immune system, in particular with the aberrant chemotaxis of cells of the immune system.

Furthermore, the invention provides pharmaceutical compositions and for the prevention and/or treatment of a disorder associated with the activity of glutaminyl cyclase and/or aberrant activity of cells of the immune system, in particular with the aberrant chemotaxis of cells of the immune system, and characterized in that they comprise an effective amount of the compound according to the invention and at least one pharmaceutically acceptable adjuvant. In some embodiments of the invention, the adjuvant is a pharmaceutically acceptable carrier and/or excipient.

The invention also includes a method for the prevention and/or treatment of a disorder associated with the activity of glutaminyl cyclase in the body comprising administering to said body a pharmaceutical composition according to the invention. Such a disorder associated with the glutaminyl cyclase activity is the disease associated with aberrant activity of cells of the immune system, in particular with the aberrant chemotaxis of cells of the immune system, particularly lung and respiratory tract disease. In certain non-limiting embodiments of the invention, the lung and respiratory tract disease is bronchial asthma, acute and chronic bronchitis, pharyngitis, pulmonary emphysema, rhinitis, rhinosinusitis, or chronic obstructive pulmonary disease. In particular cases of embodiment of the invention, the body is a human or animal.

DETAILED DESCRIPTION OF THE INVENTION

Preparation of Compounds I-X, as well as a number of other chemical compounds is described in the application for the invention RU 2013/116822. The indicated patent application discloses dicarboxylic acid bisamide derivatives which have the ability of complexing or chelating metal ions, and also the use thereof as an agents for preventing and/or treating viral hepatitis, HIV infection, cancer; neurodegenerative, cardiovascular, inflammatory diseases; diabetes, gerontological diseases, diseases caused by toxins of microorganisms, and also alcoholism, alcoholic cirrhosis, anemia, porphyria tarda, poisonings by transition metal salts.

In the course of the studies of the specific pharmacological activity of Compound of formula (A) authors of the present invention have surprisingly discovered that compounds of formula (A) affect chemotaxis of cells of the immune system. The decrease in the influx of cells of the immune system may be used in the treatment of a number of diseases associated with aberrant activity of cells of the immune system cells, in particular lung and respiratory tract diseases such as bronchial asthma, acute and chronic bronchitis, pharyngitis, rhinitis (in particular allergic rhinitis), rhinosinusitis, chronic obstructive pulmonary disease and its manifestations (in particular, pulmonary emphysema, bronchial obstruction); and also abdominal organ diseases such as Crone's disease, ulcerative colitis, peritonitises and nephropathy (particularly diabetic nephropathy); and radiation sickness.

Since the influence on the chemotaxis cannot be predicted or explained by the ability of the compound to the complexing or chelating of metal ions, an attempt was made to search for potential therapeutic targets. In the source of studies, the authors of the present invention have discovered that the observed therapeutic effect of compounds of formula (A) is associated with the ability of these compounds to inhibit the activity of glutaminyl cyclase. In the source of the following studies, the ability to inhibit the activity of glutaminyl cyclase has also been shown for compounds III, IV, V, VI, VII, VIII, IX and X.

Thus, Compounds I-X are novel glutaminyl cyclase inhibitors which have the influence on chemotaxis of cells of the immune system and may be used for the therapy of diseases associated with aberrant activity of cells of the immune system cells, in particular lung and respiratory tract diseases such as bronchial asthma, acute and chronic bronchitis, pharyngitis, rhinitis (in particular allergic rhinitis), rhinosinusitis, chronic obstructive pulmonary disease and its manifestations (in particular, pulmonary emphysema, bronchial obstruction); and also abdominal organ diseases such as Crone's disease, ulcerative colitis, peritonitises and nephropathy (particularly diabetic nephropathy); and also radiation sickness and pain syndrome.

TERMS AND DEFINITIONS

The term «Compound I» relates to N,N'-bis[2-(1H-imidazol-4-yl)ethyl]oxalamide corresponding by the following structural formula:

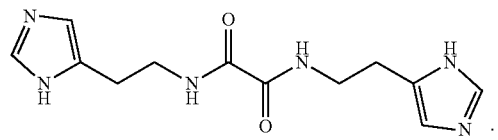

The term «Compound II» relates to N,N'-bis[2-(1H-imidazol-4-yl)ethyl]isophthalamide corresponding by the following structural formula:

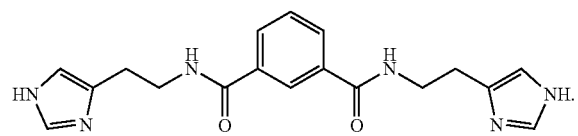

The term «Compound III» relates to N,N'-bis[2-(1H-imidazol-4-yl)ethyl]carbamide that is also represented by the structural formula:

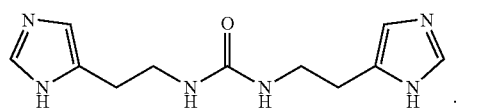

The term «Compound IV» relates to N,N'-bis[2-(1H-imidazol-4-yl)ethyl]malonamide that is also represented by the structural formula:

(IV)

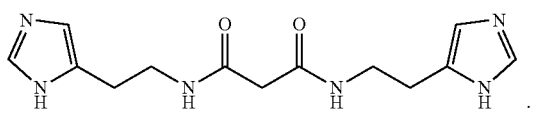

The term «Compound V» relates to N,N'-bis[2-(1H-imidazol-4-yl)ethyl]succinamide that is also represented by the structural formula:

(V)

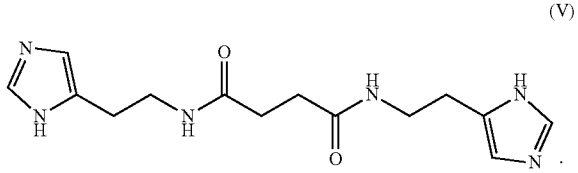 [SMILES: O=C(CCC(=O)NCCc1cnc[nH]1)NCCc1cnc[nH]1]

The term «Compound VI» relates to N,N'-bis[2-(1H-imidazol-4-yl)ethyl]glutaramide corresponding to the following structural formula:

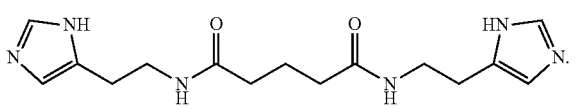 [SMILES: O=C(CCCC(=O)NCCc1cnc[nH]1)NCCc1cnc[nH]1]

The term «Compound VII» relates to N,N'-bis[2-(1H-imidazol-4-yl)ethyl]adipamide corresponding to the following structural formula:

(VI)

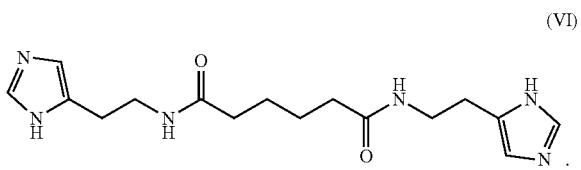 [SMILES: O=C(CCCCC(=O)NCCc1cnc[nH]1)NCCc1cnc[nH]1]

The term «Compound VIII» relates to N,N'-bis[2-(1H-imidazol-4-yl)ethyl]-3-methylpentanediamide corresponding to the following structural formula:

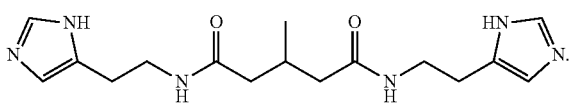 [SMILES: CC(CC(=O)NCCc1cnc[nH]1)CC(=O)NCCc1cnc[nH]1]

The term «Compound IX» relates to N,N'-bis[2-(1H-imidazol-4-yl)ethyl]-3,3-dimethylpentanediamide corresponding to the structural formula:

(IX)

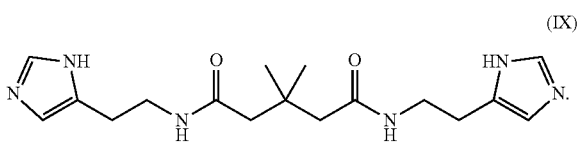 [SMILES: CC(C)(CC(=O)NCCc1cnc[nH]1)CC(=O)NCCc1cnc[nH]1]

The term «Compound X» relates to N,N'-bis[2-(1H-imidazol-4-yl)ethyl]terephthalamide corresponding to the following structural formula:

(X)

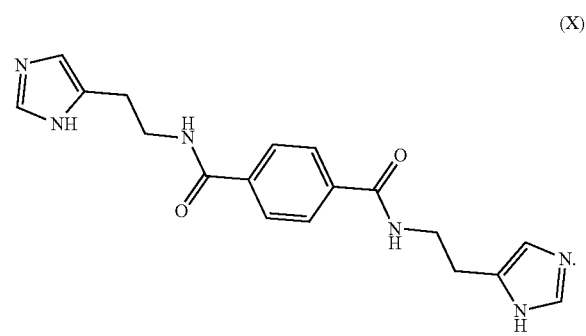 [SMILES: O=C(NCCc1cnc[nH]1)c1ccc(C(=O)NCCc2cnc[nH]2)cc1]

The term "C" when it is used with reference to a temperature means the centigrade temperature grade or the Celsius temperature scale.

The term "$IC_{50}$" means the concentration of test compound upon which the half-maximal inhibition of the enzyme is achieved.

The term "pharmaceutically acceptable salts" or "salts" includes salts of active compounds which are prepared with relatively nontoxic acids. Examples of pharmaceutically acceptable nontoxic salts include salts formed by inorganic acids such as hydrochloric, hydrobromic, phosphoric, sulfuric and perchloric acids or by organic acids such as acetic, oxalic, maleic, tartaric, succinic, citric or malonic acids, or obtained by other methods used in the art, e.g., by the ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanate, hydroiodide, 2-hydroxyethanesulfonate, lactobionate, lactate, laurate, lauryl sulfate, malate, maleate, malonate, methanesulfonate (mesylate), 2-naphthalenesulfonate, nicotinate, nitrate, oleate, oxalate, palmitate, pamoate, pectinate, persulfate, 3-phenylpropionate, phosphate, picrate, pivalate, propionate, hemifumarate, stearate, succinate, sulfate, tartrate, thiocyanate, p-toluenesulfonate (tosylate), undecanoate, valeriate, and the like.

The term "solvate" is used to describe a molecular complex comprising the compound according to the invention and one or more molecules of a pharmaceutically acceptable solvent, for example ethanol. The term "hydrate" is used when said solvent is water.

The term "aberrant activity" of cells of the immune system herein means the activity that significantly differs from the basic activity level of cells of the immune system in the body in the absence of pathology. The aberrant activity may be caused by the excess influx of cells of the immune system to the organ or tissue, the abnormality of processes resulting in the activation of cells of the immune system, the deregulation of processes associated with the death of cells of the immune system, as well as by other factors.

The term "adjuvant" means any pharmaceutically acceptable substance of an inorganic or organic origin that is the part of a medicament or is used in the process of the production, the manufacture of the medicament to impart the necessary physical and chemical properties to it.

The term "RPMI medium" (Engl. Roswell Park Memorial Institute medium) means a medium for cell and tissue cultures. RPMI is traditionally used for the cultivation of human lymphoid cells. The medium contains a substantial amount of phosphate and has the formulation for the cultivation in the atmosphere containing 5% carbon dioxide.

The term "glutaminyl cyclase" means the enzyme-aminoacyltransferase participating in the conversion of N-terminal glutamine to pyroglutamine in different peptide substrates. The formation of the N-terminal pyroglutamate protects biologically active peptides, hormones and chemokines (e.g., thyreotrophin-releasing hormone, (3-chemokine ligand-2) from the degradation by exopeptidases and in some cases may increase the affinity of ligands to their receptors.

The term "chemotaxis" means the directed movement of cells in response to a chemical stimulus. At the heart of the chemotaxis there is the ability of a cell to respond to the concentration gradient of a chemotactic mediator. The chemotaxis is the process due to which cells of the immune system leave the bloodstream and migrate to the damaged tissue. Chemotactic substances (chemoattractants) play the leading role in the chemotaxis.

One of the most potent chemoattractants for monocytes and macrophages is a chemokine CCL2.

Terms "treatment", "therapy" encompass the treatment of pathological conditions in mammals, preferably a human, and include: a) lowering, b) blocking (delay) of a disease, c) alleviating the disease severity, i.e. the induction of the disease regression, d) reversing the disease or condition to which the term applies, or one or more symptoms of the disease or condition.

The term "prophylaxis", "prevention" encompasses the elimination of risk factors, as well as the prophylactic treatment of subclinical stages of a disease in mammals, preferably in a human, directed to the reduction of the likelihood of the onset of clinical stages of the disease. Patients are selected for the preventive therapy based on factors that, based on known data, entail increased risk of the onset of clinical stages of the disease compared to the general population. The prophylactic therapy may be a) the primary prevention and b) the secondary prevention. The primary prophylaxis is defined as the prophylactic treatment for patients, in whom the clinical stage of the disease has not yet occurred. The secondary prophylaxis is the prevention of the re-occurrence of the same or similar clinical stage of the disease.

Compounds I-X are perspective for treating of diseases associated with aberrant activity of cells of the immune system, especially diseases related to aberrant chemotaxis of cells of the immune system, in particular for the treatment of lung and respiratory tract diseases such as bronchial asthma, acute and chronic bronchitis, pharyngitis, rhinitis (in particular allergic rhinitis), rhinosinusitis, chronic obstructive pulmonary disease and its manifestations (in particular, pulmonary emphysema, bronchial obstruction); abdominal organ diseases such as Crone's disease, ulcerative colitis, peritonitises and nephropathy (particularly diabetic nephropathy); radiation sickness and pain syndrome having both the systemic and local character, including provided by primary pathological changes or associated with different diseases or long intake of some medicaments. In some particular embodiments, compounds according to the invention may be used for the treatment of other diseases associated with aberrant activity of cells of the immune system.

A Method of the Therapeutic Use of the Compounds

The subject matter of the invention also includes administering to a subject in need of appropriate treatment a therapeutically effective amount of one or more compounds according to the invention. The therapeutically effective amount means such an amount of one or more compounds that is administered or delivered to a patient, wherein the patient is most likely to manifest the desired response to treatment (prophylaxis). The exact amount required amount may vary from subject to subject, depending on age, body weight and general condition of the patient, severity of disease, administration methods, the combination treatment with other drugs, etc.

Compounds according to the invention or a pharmaceutical composition comprising one or more compounds may be administered to the patient in any amount (preferably, a daily dose of the active ingredient is up to 0.5 g for a patient per day, most preferably, a daily dose is 5-50 mg/day) and by any way of the administration (preferably, the oral way of the administration), effective to treat or prevent the disease.

After mixing a medicament with a particular suitable pharmaceutically acceptable carrier in a desired dosage, compositions representing the essence of the invention may be administered to a human or other animals orally, parenterally, topically, etc.

The administration may be carried out both one-time and several times a day, a week (or any other time interval), or from time to time. Furthermore, one or more compounds may be administered to the patient daily over a particular period of days (e.g., 2-10 days), followed by a period without receiving the substance (e.g., 1-30 days).

In the case where the compounds according to the invention is used as the part of a regimen of the combination therapy, the dose of each component of the combination therapy is administered for a required treatment period. Compounds constituting the combination therapy may be administered to a patient both at a time in the dosage form, containing all components and in the form of individual dosages of the components.

Pharmaceutical Compositions

The invention also relates to pharmaceutical compositions comprising a compound of formula (A), in particular compounds I-X (or a prodrug form or other pharmaceutically acceptable derivative) and one or more pharmaceutically acceptable carriers, adjuvants, diluents and/or excipients, such as may be administered to the patient together with the compound representing the essence of the invention and which do not affect the pharmacological activity of the compound, and are nontoxic when administered in doses sufficient to delivery of a therapeutic amount of the compound.

Pharmaceutical compositions claimed according to the present invention comprise one or more compounds of formula (A) together with pharmaceutically acceptable carriers that may include any solvents, diluents, dispersions or suspensions, surfactants, isotonic agents, thickeners and emulsifiers, preservatives, binders, lubricants, etc., suitable for the particular dosage form. Materials that may serve as pharmaceutically acceptable carriers include, but are not limited to, mono- and oligosaccharides and their derivatives; gelatin; talc; excipients such as cocoa butter and suppository waxes; oils such as peanut, cottonseed, safflower, sesame, olive, corn, and soybean oil; glycols such as propylene glycol; esters such as ethyl oleate and ethyl laurate; agar; buffering agents such as magnesium hydroxide and aluminum hydroxide; alginic acid; pyrogen-free water; isotonic solution, Ringer's solution; ethyl alcohol, and phosphate buffer solutions. The composition may also comprise other nontoxic compatible lubricants such as sodium lauryl sulfate and magnesium stearate, and also dyes, film formers, sweeteners, flavoring and perfuming agents, preservatives and antioxidants.

The object of the invention are also dosage forms—a class of pharmaceutical compositions, the formulation of which is optimized for a particular way of the administration to the body in a therapeutically effective dose, e.g., for oral, topical administration, or the administration by inhalation, e.g., in the form of the inhalation spray, or by intravascular method, intranasally, subcutaneously, intramuscularly, as well as by infusion method, in the recommended dosages.

Dosage forms of the invention may comprise formulations obtained by methods of the use of liposomes, microencapsulation techniques, methods of the preparation of nanoforms of the medicament or other methods known in the pharmaceutics.

Upon the preparation of the composition, for example in the form of a tablet, an active principle is mixed with one or more pharmaceutical excipients such as gelatin, starch, lactose, magnesium stearate, talc, silica, gum arabic, mannitol, microcrystalline cellulose, hypromellose or the like.

The tablets may be coated with sucrose, a cellulose derivative or with other substances suitable for applying a coating. The tablets may be prepared by various methods such as direct compression, dry or wet granulation or hot fusion in the hot state.

A pharmaceutical composition in the form of a gelatin capsule may be prepared by mixing the active principle with other substances, and filling soft or solid capsules with the obtained mixture.

For the parenteral administration, aqueous suspensions, isotonic saline solutions or sterile solutions for injections, which contain pharmacologically compatible agents, for example propylene glycol or butylene glycol, are used.

Examples of Pharmaceutical Compositions

Compounds of formula (A) described in the invention may be used for the prevention and/or treatment of human diseases or animal diseases in the form of the following compositions (Compound of formula (A) is meant under the "Substance"):

| Tablet I | mg/tablet |
|---|---|
| Substance | 0.5 |
| Microcrystalline cellulose | 66.5 |
| Sodium carboxymethyl starch | 2.3 |
| Magnesium stearate | 0.7 |

| Tablet II | mg/tablet |
|---|---|
| Substance | 5.0 |
| Microcrystalline cellulose | 62.0 |
| Sodium carboxymethyl starch | 2.3 |
| Magnesium stearate | 0.7 |

| Tablet III | mg/tablet |
|---|---|
| Substance | 50 |
| Microcrystalline cellulose | 620 |
| Sodium carboxymethyl starch | 23 |
| Magnesium stearate | 7 |

| Tablet IV | mg/tablet |
|---|---|
| Substance | 50 |
| Lactose Ph. Eur | 223.75 |
| Sodium croscarmellose | 6.0 |
| Corn starch | 15 |
| Polyvinyl pyrrolidone (5% v. paste) | 2.25 |
| Magnesium stearate | 3.0 |

| Tablet V | mg/tablet |
|---|---|
| Substance | 200 |
| Lactose Ph. Eur | 182.75 |
| Sodium croscarmellose | 12.0 |
| Corn starch (5% v. paste) | 2.25 |
| Magnesium stearate | 3.0 |

| Capsule | mg/capsule |
|---|---|
| Substance | 10 |
| Lactose Ph. Eur | 488.5 |
| Magnesia | 1.5 |

| Formulation for injections I | (50 mg/ml) |
|---|---|
| Substance | 5.0% w/v |
| 1M solution of sodium hydroxide | 15.0% w/v |
| 1M solution of sulphuric acid | up to pH 7.6 |
| Polyethylene glycol 400 | 4.5% w/v |
| Water for injections | up to 100% |

| Ointment | ml |
|---|---|
| Substance | 40 mg |
| Ethanol | 300 µl |
| Water | 300 µl |
| 1-dodecylazacycloheptanone | 50 µl |
| Propylene glycol | up to 1 ml |

These compositions may be prepared in accordance with standard pharmaceutical techniques. Tablets (I)-(II) may be coated by the enteric shell, using, for example, cellulose acetate phthalate.

Use of Compounds I-X in Combination Therapy

Despite the fact that Compounds I-X may be administered as an individual active pharmaceutical agent, it may also be used in combination with one or more other agents, in particular, the other agent may be an antibiotic, NSAIDs or other anti-inflammatory agent, antihypertensive agent, glucocorticosteroid, a monoclonal antibody, etc. In case of the combination intake, therapeutic agents may represent different dosage forms that are administered simultaneously or sequentially at different times, or the therapeutic agents may be combined in one dosage form.

The phrase "combination therapy" with respect to the compounds of the invention in combination with other pharmaceutical agents is sequential or simultaneous intake of all agents that somehow provides the beneficial effect of the combination of drugs. The combined administration means, in particular, the combined delivery, e.g. in one tablet, capsule, injection or in the other form having a fixed ratio of active substances, as well as the simultaneous delivery in several separate dosage forms for each compound respectively.

Thus, the administration of compounds I-X of the invention may be carried together with additional therapies known to those skilled in the field of the prevention and treatment of corresponding diseases, including the use of antibacterial, cytostatic and cytotoxic drugs, medicaments for inhibiting symptoms or side effects of one of medicaments.

If the medicament is a fixed dose, such combination uses the compounds of the invention in a suitable dosage range. Compounds I-X according to the invention may also be administered to the patient sequentially with other agents, in the case where the combination of these medicaments is not possible. The invention is not limited to the sequence of administration; the compounds of the invention may be administered to the patient together, before or after the administration of another medicament.

EXAMPLES

The Obtainment of Compounds According to the Invention

Methods of producing Compounds I-X are disclosed in application for the invention RU 2013/116822. The ability of similar compounds of complexing or chelating metal ions is described in the same application.

The Characteristic of the Biological Activity of Compounds According to the Invention The biological activity of Compounds I-X has been studied in different in vitro and in vivo experiments. In particular, the study of the activity of Compounds I and II in various in vitro and in vivo models have shown an inhibitory effect of Compounds I and II on the chemotaxis of monocytes, macrophages and other immune system cells. The biological effect of Compounds I and II cannot be predicted or explained on the basis of prior knowledge about the ability of Compounds I and II of the chelation of metal ions.

Studies of the biological activity of Compounds III-X in vitro have revealed that Compounds III-X are also inhibitors of the enzyme-glutaminyl cyclase and thus the effect of Compounds III-X on the chemotaxis of cells of the immune system may be mediated by the inhibition of the activity of glutaminyl cyclase.

The Study of the Effect of Compounds I-X on the Enzymatic Activity of Human Glutaminyl Cyclase In Vitro During studies of the effect of Compounds I-X, which are the object of the present invention, on the enzymatic activity of glutaminyl cyclase in vitro, the direct inhibitory effect of Compounds I-X on recombinant intracellular human glutaminyl cyclase first has been found.

The glutaminyl cyclase activity at various concentrations of Compounds I-X has been studied at 25° C. with the use of a fluorescent substrate L-glutaminyl 2-naphthyl amide (Gln-bNA) (Anal Biochem. 2002 Apr. 1; 303(1):49-56). The reaction mixture having a volume of 100-µl has contained 50 µM of fluorogenic substrate; ~0.2 units of human pyroglutaminyl aminopeptidase (1 unit is defined as an amount hydrolyzing 1 micromole of pGlu-bNA per minute), and an aliquot of the recombinant intracellular human glutaminyl cyclase (gQC) in 50 mM trisaminomethane-HCl and 5% glycerol, a pH is 8.0. The reaction was initiated by adding to the reaction mixture an aliquot of glutaminyl cyclase incubated with Compounds I-X for 5 minutes.

TABLE 1

| The effect of Compounds I-X on the enzymatic activity of human glutaminyl cyclase in vitro. | | | |
| --- | --- | --- | --- |
| No | Compound | IC50, µM | Ki, µM |
| I | 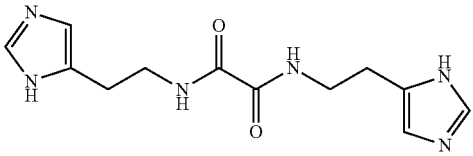 [SMILES: O=C(NCCc1cnc[nH]1)C(=O)NCCc1cnc[nH]1] | 1.4 | 0.8 |
| II | 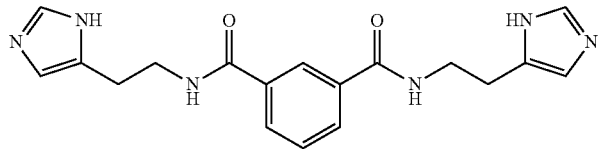 [SMILES: O=C(NCCc1cnc[nH]1)c1cccc(C(=O)NCCc2cnc[nH]2)c1] | 2.9 | 1.61 |
| III | 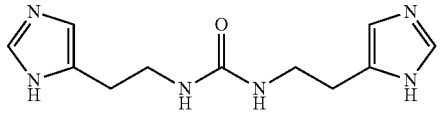 [SMILES: O=C(NCCc1cnc[nH]1)NCCc1cnc[nH]1] | 3.5 | 2 |

TABLE 1-continued

The effect of Compounds I-X on the enzymatic activity of human glutaminyl cyclase in vitro.

| No | Compound | IC50, µM | Ki, µM |
|---|---|---|---|
| IV | | 6.3 | 3.50 |
| V | | 20 | 11 |
| VI | | 5.4 | 3 |
| VII | | 4.4 | 2 |
| VIII | | 7.3 | 4 |
| IX | | 5.7 | 3.17 |
| X | | 0.8 | 0.44 |

The further course of the reaction was monitored spectrophotometrically (the wavelength of the excitation and emission were 320 and 410 nm). The enzyme activity was determined by an amount of the released 2-naphthyl amide (bNA), calculated from the calibration curve. The IC50 values were calculated using nonlinear regression of "inhibitor concentration"-"enzymatic activity" curve. As a reference substance, the known inhibitor of glutaminyl cyclases—compound PBD150—has been used (J Med Chem. 2006 Jan. 26; 49(2): 664-77).

As the result of the study, it has been established that Compounds I-X inhibit the activity of glutaminyl cyclase ranging from 0.8 to 20 µM (see Table 1).

Study of the Effect of Compounds I and II on the Migration of Monocytes In Vitro The effect of Compounds I and II on the migration of monocytes in vitro has been studied with the use of cells of line U937 bred to the concentration of $(2-3) \times 10^6$ cells/ml on the medium RPMI 1640 with the addition of 10% thermo-inactivated fetal bovine serum (Biochem J. 2012 Mar. 1; 442(2):403-12). About $1 \times 10^7$ U937 cells were incubated with different concentrations of Compounds I and II (7 concentrations for each of compounds at all) at 37° C. for 2 hours and then were treated with lipopolysaccharide E. coli (O111:B4). A supernatant (the conditioned medium) has been used for studying the migration of monocytes.

A fresh batch of U937 cells has been colored by the fluorescent dye Calcein AM for 1 hour at 7° C. After this, the aliquot of the colored cells has placed to the upper section of holes of plane-table BD Falcon™ HTS FluoroBlok, the cells of which are separated by optically opaque semipermeable membranes. The conditioned medium obtained after the incubation of cells with the inhibitor and lipopolysaccharide has been placed to the bottom section of holes of the plane-table. The plane-tables have been incubated for 2 hours at 37° C., an amount (% in respect to the study without the inhibitor) of cells migrated to the bottom section of holes was fluorimetrically determined. As a reference substance, the known inhibitor of glutaminyl cyclases—compound PBD150—has been used (J Med Chem. 2006 Jan. 26; 49(2):664-77).

It has been established as the result of the experiment that Compound I and Compound II in the micromolar range of concentrations has the inhibitory effect on the migration of monocytes in vitro. Compound I inhibits the migration of monocytes in a wide range of concentrations from 1 µM to 300 µM with the efficacy close to 60%. In the same range of concentrations, Compound II inhibits the migration of monocytes with the efficacy of 50-70%

Study of the Effect of Compound I on the Chemotaxis of Leucocytes In Vivo on The Bronchial Asthma Model in Guinea Pigs The induction of bronchial asthma in guinea pigs were performed according to the standard procedure (Current Drug Targets. 2008 June; 9(6):452-65). Animals were immunized by a single intraperitoneal injection of 0.5 ml solution containing 100 µg/ml ovalbumin (Sigma) and 100 mg/ml hydroxyaluminum. Intact animals were intraperitoneally injected with a saline solution in a volume of 0.5 ml.

At 29, 30 and 31 day of the experiment, the provocation of hyperreactivity of respiratory tracts was carried out by the inhalation administration of ovalbumin in increasing concentrations—0.1, 0.3 and 0.5 mg/mL (at 29, 30 and 31 day respectively). The inhalation was performed for 5 minutes or until the appearance of apparent signs of asphyxia (sideways incidence). On the $32^{nd}$ day, animals were administered with a challenging dose of ovalbumin—1 mg/ml for 5 minutes with the estimation of bronchospastic reaction.

The test compound was intragastrically administered to animals daily once a day for 10 days, finishing before 24 hours prior the administration of the challenging dose of an antigen.

24 hours after the administration of the challenging dose of ovalbumin bronchoalveolar lavage (BAL) was collected from animals. The BAL taking was performed under anesthesia by washing lungs with 5 ml of saline solution prewarmed to 37° C. via the trachea using a syringe dispenser.

In the bronchoalveolar lavage fluid, the absolute count of cellular elements in 1 µl of the lavage was calculated using Goryaev's camera. Then, the bronchoalveolar lavage was centrifuged at 200 g for 10 minutes. Smears were prepared from the cell sediment, which smears were further fixed in methanol and stained by Romanowsky-Giemsa for counting endopulmonary cytogram.

The cytological analysis of the bronchoalveolar lavage (BAL) has revealed the multiple increase in cellular elements in the BAL of sensibilized guinea pigs (FIG. 1). Thus, the model is characterized by the inflammatory response of the respiratory tract of experimental animals. The analysis of individual cell types has shown that the most pronounced influx of cells is to eosinophils. The obtained results confirm literature data and allow to conclude that the simulated inflammation is allergic.

The daily intragastric administration of Compound I for 10 days has reduced the influx of inflammatory cells in the bronchoalveolar space. Compound I has a therapeutic effect throughout the dose range under study (0.14-14 mg/kg), has reduced both the total number of leukocytes and the quantity of individual cell types: eosinophils, neutrophils, macrophages (FIG. 1).

Thus, in FIG. 1, a symbol * designates distinctions which are statistically significant compared to the intact group (p<0.05); and a symbol &—distinctions which are statistically significant compared to the control group (p<0.05).

The obtained results indicate that Compound I has the expressed therapeutic effect on the bronchial asthma.

Study of the Effect of Compound I on the Chemotaxis of Macrophages, Neutrophils, and Eosinophils In Vivo on a Rat Model of Non-Infectious Pulmonary Inflammation The ret model of sephadex-induced pulmonary bronchitis was realized by the standard procedure (Int Arch Allergy Immunol. 2011; 154(4):286-94). Wistar male rats were singly administered by inhalation with Sephadex G-200 (Pharmacia, Sweden) in a dose of 5 mg/kg. Test compounds were intragastrically administered to the animals fourfold: 24 hours and 1 hour prior to and 24 and 45 hours after the administration of sephadex. The reference medicament budesonide was administered in the same way by inhalation in a dose of 0.5 mg/kg. After 48 hours after the inhalation with sephadex, the taking of the bronchoalveolar lavage was performed. In the lavage the total number of leukocytes was evaluated and leukocytic formula was determined.

The analysis of the bronchoalveolar lavage has shown that the single inhaled administration of sephadex G-200 to rats causes the marked influx of leukocytes into the lung. The quantity of all cell types was increased in the control group compared to intact groups (Table 2).

TABLE 2

A quantity of cell elements in bronchoalveolar lavage on the model of sephadex-induced bronchitis in rates (M ± m, n = 10)

| Group | A quantity of cell elements in 1 µl of the BAL | | | | |
|---|---|---|---|---|---|
| | Leukocytes | Neutrophils | Eosinophils | Macrophages | Lymphocytes |
| Intact | 2209 ± 348 | 270 ± 54 | 0 ± 0 | 1975 ± 346 | 0 ± 0 |
| Control | 4617 ± 582* | 989 ± 135* | 248 ± 65* | 3209 ± 397* | 0 ± 0 |
| Compound I (0.18 mg/kg) | 3833 ± 525* | 283 ± 75 & | 0 ± 0 & | 3127 ± 351* | 0 ± 0 |
| Compound I (1.8 mg/kg) | 4133 ± 454* | 846 ± 101* | 0 ± 0 & | 3287 ± 381* | 0 ± 0 |

Notes:
*the distinction from the intact group according to Student's t-test at p < 0.05;
& the distinction from the control group according to Student's t-test at p < 0.05.

The intragastric administration of Compound I to rats has reduced the content of neutrophils and eosinophils in the BAL to the level of intact animals. The obtained results indicate that Compound I has a therapeutic effect in case of the inflammation of lower respiratory tract, in particular bronchitis.

The Study of the Activity of Compound I on the Model of Non-Infectious Pneumonia Induced by Cigarette Smoke Extract The induction of non-infectious pneumonia in mice was carried out according to the standard procedure [Exp Lung Res. 2013 February; 39(1):18-31]. Male Balb/c mice were intraperitoneally administered with cigarette smoke extract (CSE, 0.45 ml/20 mg) at 0, $11^{th}$, $15^{th}$, $17^{th}$, $19^{th}$ and $22^{nd}$ day. The CSE was prepared as follows: 5 cigarettes were burnt, using a vacuum pump, the smoke was filtered to remove particles and collected in a vessel containing a phosphate saline buffer. Compound I was administered intragastrically, daily, once a day from 7th to 27th day. Euthanasia was carried out on the $28^{th}$ day. The right lung lobe was fixed in 10% neutral formalin solution, passed through the alcohols of ascending concentrations to xylene, and embedded in paraffin by standard procedures. Deparaffinated 5-micron shears were stained with hematoxylin-eosin and the histological analysis was carried out.

Each lesion was evaluated according to a 5-point scale: 1 point—the inflammatory infiltrate occupies 0-20% of the area of the histological preparation under study, 2 point—the inflammatory infiltrate occupies 21-40% of the area of the histological preparation under study, 3 points—the inflammatory infiltrate occupies 41-60% of the area of the histological preparation under study, 4 points—the inflammatory infiltrate occupies 61-80% of the area of the histological preparation under study, 5 points—the inflammatory infiltrate occupies 81-100% of the area of the histological preparation under study. Alveolar destruction index (DI) as the percentage of the damaged alveoli relative to the total number of alveoli was also calculated.

The results of the study showed that multiple intraperitoneal administration of the cigarette smoke extract to mice induces the formation of perivasculitis, peribronchitis, alveolitis and interstitial pneumonia (Table 3).

The intragastric administration of Compound I significantly reduced the development of perivasculitis, peribronchitis, alveolitis and interstitial pneumonia (Table 3). The obtained results make it possible to conclude that Compound I will have the therapeutic effect in case of perivasculitis and alveolitis.

Study of the Activity of Compound I In Vivo on a Mouse Model of Pulmonary Emphysema The inflammation and pulmonary emphysema have caused by a single endotracheal injection of porcine pancreatic elastase. The elastase was endotracheally administered once in a dose of 0.6 U/mouse in 30 µl NaCl 0.9%. Pentobarbital has been intraperitoneally used for the anesthesia during the operation in a dose of 30 mg/kg. The operative site has been treated with 70% ethanol solution and has been released from hair-covering.

By the median line of neck, the skin, subcutis and the own fascia of the neck has been dissected. Muscles have been moved apart by a blunt dissection tissue method on the ventral side of trachea.

The injection of porcine pancreatic elastase has been carried out using a Hamilton syringe along the wind flow during inhalation. After the wound closure the operative site was treated with an antiseptic. The administration of elastase was taken as day 0 of the experiment.

Compound I was intragastrically administered in a dose of 0.3 mg/kg daily once a day on the $8^{th}$-$21^{st}$ day of the experiment. On the $21^{st}$ day the animal were euthanized in a $CO_2$ chamber and lungs were separated. To assess the dynamics and severity of emphysema in the lung tissue of the left lung, histologic specimens were made. To do this, the lung was fixed in 10% solution of neutral formalin and then is embedded in paraffin according to the standard procedure. Specimens of the apex of lung, medium lung filed and lower lung field having a thickness of 5 microns have been obtained from deparaffinized shears and stained with hematoxylin and eosin by the standard procedure. Next the photos of the apex of lung, the middle and lower lung fields were made. Using computer graphics processing tools, the localization and the area of the extended emphysematous lung tissue (% of normal tissue) were studied, vessels and bronchi were excluded from the calculation (Int J Biomed Imaging. 2012; 2012:734734; Front Physiol. 2015 May 12; 6:14).

The histological examination at $21^{st}$ day after the administration of elastase in all the areas of the lung of mice, the moderately pronounced hyperemia of vessels of microcircular channel and capillaries of interalveolar septa was revealed. Furthermore, elastase resulted in thickening of alveolar walls due to the lympho-macrophage infiltration and also the inflammatory infiltration of the interstitial tissue. The lumen of individual alveoli is also filled with macrophages and lymphocytes. As a result of the effect of the damaging agent on elastic fibers of bronchioles, alveolar ducts and alveoli in the lung parenchyma, the alveolar distension and disruptions of alveolar septa was observed, the diffuse emphysema was developed. The analysis of the

TABLE 3

Results of the histological study on the model of non-infectious pneumonia induced by cigarette smoke extract (M ± m, n = 12)

| Group | A dose of compound, mg/kg | Perivasculitis, points | Peribronchitis, points | Alveolitis (DI, %) | Interstitial pneumonia, points |
|---|---|---|---|---|---|
| Intact | — | 0.71 ± 0.20 | 0.51 ± 0.19 | 11.50 ± 1.20 | 0.99 ± 0.20 |
| Control | — | 1.50 ± 0.24* | 1.29 ± 0.18 | 30.90 ± 2.30* | 1.81 ± 0.27* |
| Compound I | 0.3 | 0.38 ± 0.13& | 1.09 ± 0.24 | 17.70 ± 2.00*& | 1.08 ± 0.26 |

Notes:
*the distinction from the intact group according to Student's t-test at $p < 0.05$;
&the distinction from the control group according to Student's t-test at $p < 0.05$.

specimens has shown that on the 21st day of the experiment, a significant portion of the left lung tissue was busy with extended emphysematous alveoli with the destruction of interalveolar septa. The emphysema was localized in all lung fields. The most pronounced lesions were observed in the lower lung field (table 4).

TABLE 4

The area of extended emphysematous ling tissue (% of normal) in mice under conditions of intratracheal administration of elastase at the $21^{st}$ day of the experiment (M ± m, n = 5)

| Groups | Top pulmonary field | Medium pulmonary field | Lower pulmonary field |
|---|---|---|---|
| Intact control | 0 | 0 | 0 |
| Pathological control | 24.06 ± 6.12* | 63.76 ± 5.02* | 82.90 ± 2.88* |
| Compound I (3 mg/kg) | 11.76 ± 1.48* | 37.09 ± 5.86*● | 35.28 ± 5.81*● |

Notes:
1 - *distinctions are reliable as compared to intact control ($p < 0.05$);
2 - ●distinctions are reliable as compared to pathological control ($p < 0.05$).

The administration of Compound I has reduced the intensity of the inflammatory infiltration of the lung parenchyma and the pronounced hyperemia of vessels of microcircular channel and capillaries of interalveolar septa, has decreased the relative area of extended emphysematous alveoli as compared to the group of the pathological control (table 4). The obtained data provide ground to conclude that Compound I has the therapeutic effect in case of pulmonary emphysema.

The Study of Therapeutic Activity of Compound 1 on the COPD Model in Guinea Pigs The study was conducted on male guinea pigs. The chronic obstructive pulmonary disease has been caused by the endotracheal administration of E. coli cell wall lipopolysaccharide (LPS) and tobacco smoke extract (TSE) Biol Pharm Bull. 2009 September; 32(9):1559-64). The TSE has been prepared from Hi-Lite cigarettes (Japan) (the formulation of 1 cigarette: tar 17 mg/cig, nicotine 1.4 mg/cig). Before the preparation of the extract, a cigarette filter has been removed, the length of the cigarette with filter is 80 mm, while the filter is removed—55 mm. The extraction has been performed by pulling the smoke of the lit cigarette through the PBS with a constant speed, using a vacuum pump (40 ml/40 cigarettes). A time of burning one cigarette was 180 seconds. To remove particles, the resulting extract was filtered through a bacterial filter with a pore size of 45 nm. The TSE was inhaled to guinea pigs (0.3 ml/min, 40 min) daily once a day at 1-4, 6-9, 11-14, 16-19 hours. The LPS was inhaled to guinea pigs (25 µg/ml, 0.3 ml/min, 1 hour) once a day on the $5^{th}$, $10^{th}$ and $15^{th}$ day. Before the last inhalation of the TSE, immediately after the last inhalation of the TSE and 1.5 hours after the last inhalation of the TSE, the respiratory function was assessed (for 15 minutes). Immediately after assessing the respiratory function, bronchoalveolar lavage (BAL) was collected. The BAL capture was performed under anesthesia by washing the lungs with 5 ml of saline solution heated up to 37° C. through the trachea using a syringe dispenser.

In the bronchoalveolar lavage fluid, the absolute count of cellular elements in 1 µl of the lavage (cytosis) was calculated using Goryaev's camera. Then, the BAL was centrifuged at 200 g for 10 minutes. Smears were prepared from the cell sediment, which smears were further fixed in methanol and stained by Romanovsky-Giemsa for counting endopulmonary cytogram.

Compound I was intragastrically administered to the animals daily once a day on the 10-$19^{th}$ day of the study (the last administration—1 hour before the last inhalation of the TSE). The false pathology group was inhaled by saline solution solution instead of TSE and LPS. Control animals instead of the test substance received a solvent in an equivalent volume.

The conducted study has shown that on the COPD model Compound 1 reduces the influx of inflammatory cells into the bronchoalveolar space of guinea pigs. Compound I is most pronounced to reduce the influx of neutrophils, macrophages, and eosinophils (Table 5).

TABLE 5

A quantity of cellular elements in the bronchoalveolar lavage on the COPD model in guinea pigs (M ± m, n = 10)

| | The quantity of cellular elements in 1 µl of the bronchoalveolar lavage | | | | |
|---|---|---|---|---|---|
| Groups | Leukocytes | Neutropils | Eosinophils | Macrophages | Lymphocytes |
| False pathology | 2488 ± 154 | 2876 ± 27 | 184 ± 65 | 2016 ± 120 | 48 ± 15 |
| Control | 7925 ± 1458# | 1632 ± 319# | 676 ± 187# | 4789 ± 782# | 168 ± 60 |
| Compound I (0.014 mg/kg) | 2748 ± 174& | 684 ± 62#& | 171 ± 32& | 1805 ± 123#& | 88 ± 29 |
| Compound I (0.14 mg/kg) | 3422 ± 434& | 937 ± 141# | 287 ± 64 # | 2064 ± 313& | 134 ± 60 |
| Compound I (1.4 mg/kg) | 4149 ± 357#& | 931 ± 166# | 245 ± 55# | 2820 ± 273& | 71 ± 29 |

Notes:
*the distinction from the false pathology group according to Student's t-test at $p < 0.05$;
&the distinction from the control group according to Student's t-test at $p < 0.05$.

Summarizing the obtained results, it is possible to conclude that Compound II has the pronounced therapeutic effect in case of COPD.

Study of the Activity of Compound I In Vivo on a Guinea Pig Model of Allergic Rhinitis A model of allergic rhinitis was realized by the standard method (Int Immunopharmacol. 2013 September; 17(1):18-25). Guinea pigs (250-300 gramms) were immunized by 4-fold (on the 0, $7^{th}$, $14^{th}$ and $21^{st}$ day) by the intraperitoneal injection of a mixture of ovalbumin (100 µg/pig) and aluminum hydroxide (5 mg/pig) diluted and suspended in the saline solution. On the $28^{th}$ day of the study, an ovalbumin solution (60 mg/ml) was iuntranasally administered to the animals by 20 µl into each nostril. On the $35^{th}$ day, the animals were intracutaneously injected with the ovalbumin solution (200 µg/ml, 25 µl), after preliminary shaving clean a skin area on the back. The confirmation of the presence of the sensibilization was the formation of edema and redness at the injection site. On the $42^{nd}$ day of the study, the intranasal administration of the ovalbumin solution (60 mg/ml, 20 µl/nostril) was performed. In order to control the formation of the allergic inflammation in particular, a group of falsely immunized animals was formed: on 0, $7^{th}$, $14^{th}$, and $21^{st}$ day pigs have received an aluminum hydroxide solution (5 mg /pig); on the $28^{th}$ day—saline solution solution, on the $42^{nd}$ day—ovalbumin (60 mg/ml, 20 µl/nostril).

Compounds I, III, IV (0.14, 1.4 mg/kg) were intragastrically administered to animals once, 3 hours before the last intranasal administration of ovalbumin. For 2 hours after the last administration of ovalbumin, the clinical manifestations of rhinitis were evaluated: a quantity of sneezes and scratchings of the nose were counted.

The research results are presented in tables 6-8.

The accounting for the clinical manifestations of allergic rhinitis for 2 hours after the last intranasal administration of ovalbumin to animals has shown the pronounced increase in experimental animals in the quantity of sneezes and scratchings of the nose, which indicates the correctness of the implemented model of allergic rhinitis.

TABLE 6

Clinical manifestations of allergic rhinitis in guinea pigs upon the therapy of animals with Compound I (M ± m, n = 10)

| Group | A quantity of sneezes/ 2 hours | A quantity of scratchings of the nose/2 hours |
|---|---|---|
| False immunization | 5.9 ± 1.3 | 12.5 ± 3.1 |
| Control | 17 ± 1.8* | 69 ± 7.4* |
| Compound I (0.14 mg/kg) | 9.3 ± 1.7 | 37.3 ± 7.8*& |
| Compound I (1.4 mg/kg) | 12.1 ± 1.5 | 41.0 ± 12.0 |

Notes:
*the distinction from the intact group according to Student's t-test at p < 0.05;
&the distinction from the control group according to Student's t-test at p < 0.05.

TABLE 7

Clinical manifestations of allergic rhinitis in guinea pigs upon the therapy of animals with Compound III (M ± m, n = 10)

| Group | A quantity of sneezes/ 2 hours | A quantity of scratchings of the nose/2 hours |
|---|---|---|
| False immunization | 5.9 ± 0.3 | 10.3 ± 2.2 |
| Control | 20.6 ± 0.9* | 75.4 ± 6.5* |

TABLE 7-continued

Clinical manifestations of allergic rhinitis in guinea pigs upon the therapy of animals with Compound III (M ± m, n = 10)

| Group | A quantity of sneezes/ 2 hours | A quantity of scratchings of the nose/2 hours |
|---|---|---|
| Compound III (0.14 mg/kg) | 17.8 ± 0.7*& | 32.5 ± 8.0*& |
| Compound III (1.4 mg/kg) | 19.0 ± 1.1* | 39.9 ± 9.5*& |

TABLE 8

Clinical manifestations of allergic rhinitis in guinea pigs upon the therapy of animals with Compound IV (M ± m, n = 10)

| Group | A quantity of sneezes/ 2 hours | A quantity of scratchings of the nose/2 hours |
|---|---|---|
| False immunization | 3.2 ± 1.06 | 6.5 ± 2.33 |
| Control | 15.2 ± 2.1* | 20.8 ± 4.2* |
| Compound IV (0.14 mg/kg) | 1.4 ± 0.67 & | 5.3 ± 1.14 |
| Compound IV (1.4 mg/kg) | 1.4 ± 0.6 & | 1.8 ± 1& |

The intragastric administration of Compounds I, III, IV to guinea pigs has markedly reduced the quantity of clinical manifestations of rhinitis. The obtained results provide grounds to conclude that Compounds I, III, IV have the pronounced therapeutic effect in case of allergic rhinitis.

The Study of the Activity of Compound I In Vivo on a Rat Model of Formalin-Induced Acute Rhinosinusitis The induction of acute rhinosinusitis was performed in male Wistar rats by the intranasal administration of 20 µl of 7.5% formalin into each nasal passage. Compound I was administered in doses of 1.8 mg/kg and 18 mg/kg daily once a day, starting 24 hours after the administration of formalin, the last administration occurred on the $7^{th}$ day. Dexamethasone (0.6 mg/kg) was administered in the same mode. On the $8^{th}$ day, the nasal lavage was collected. In the nasal lavage, the total quantity of leukocytes was assessed and the leukocyte formula was determined.

The analysis of the nasal lavage has shown that acute rhinosinusitis is accompanied by athe pronounced influx of leukocytes into the nasal cavity. The maximum increase was noted in relation to the quantity of macrophages (Table 9).

The intragastric administration of the test compound to rats has reduced the content of macrophages and neutrophils in the nasal lavage to the level of intact animals. In terms of intensity of the effect, Compound I was equalled to dexamethasone (Table 9).

TABLE 9

A quantity of cellular elements in the nasal lavage of rats on the model of acute rhinosinusitis (M ± m, n = 10)

| | A quantity of cellular elements in 1 µl of the nasal lavage | | | | |
|---|---|---|---|---|---|
| Group | Leukocytes | Neutrophils | Eosinophils | Macrophages | Lymphocytes |
| Intact | 3420 ± 641 | 3313 ± 632 | 7 ± 5 | 67 ± 16 | 0 ± 0 |
| Control | 5568 ± 1015 | 5217 ± 980 | 16 ± 10 | 291 ± 72* | 0 ± 0 |
| Compound I (1.8 mg/kg) | 5410 ± 1143 | 5132 ± 1096 | 11 ± 11 | 231 ± 49* | 0 ± 0 |

TABLE 9-continued

A quantity of cellular elements in the nasal lavage of rats on the model of acute rhinosinusitis (M ± m, n = 10)

| Group | A quantity of cellular elements in 1 µl of the nasal lavage | | | | |
|---|---|---|---|---|---|
| | Leukocytes | Neutrophils | Eosinophils | Macrophages | Lymphocytes |
| Compound I (18 mg/kg) | 2490 ± 339& | 2461 ± 339& | 0 ± 0 | 28 ± 7& | 0 ± 0 |
| Dexamethasone (0.6 mg/kg) | 1735 ± 451*& | 1664 ± 433*& | 0 ± 0 | 68 ± 23& | 0 ± 0 |

Notes:
*the distinction from the intact group according to Student's t-test at $p < 0.05$;
&the distinction from the control group according to Student's t-test at $p < 0.05$.

Thus, the obtained results have shown that Compound I has the pronounced therapeutic effect in case of rhinosinusitis.

The Study of the Activity of Compound I In Vivo on a Rat Model of Non-Infectious Pharyngitis The model of non-infectious pharyngitis was implemented on male Wistar rats. The rats were anesthetized with sodium thiopentone (50 mg/kg, intraperitoneally) and a cannula with a RenaSil® silicone rubber tube (SIL 037, Braintree Scientific, Inc., Braintree, Mass.) was inserted into the external jugular vein using a heparinized saline solution (40 U/ml).

The Evans Blue dye (Evans Blue, EB) (30 mg/kg) was administered to all the animals intravenously through a catheter; 10 minutes after the EB dye was administered, a 30% formalin solution was applied to the surface of the pharyngeal mucosa as follows: the tongue was slightly pulled out, the pharyngeal area was opened deep in the mouth with blunt forceps and gently, using a sterile cotton pad, the formation solution (50 µl) was applied for 5 seconds each time it is applied. In the intact group thephysiologicla solution was used.

60 minutes after the application of 30% formalin solution, the animals were euthanized by the exsanguination. The head of each rat was perfused with the heparinized saline solution (40 U/ml) to remove the intravascular EB dye.

The degree of the inflammation was assessed by the exudation test of the Evans blue (EB) dye. The EB dye from the tissue was extracted into formamide at 55° C. for 24 hours, and the absorption was spectrophotometrically determined at 620 nm. The amount of dye in the fabric was calculated using the standard curve for the Evans blue dye, and was expressed in micrograms of the dye per gram of wet fabric weight (µg/g).

Compound I was intragastrically administered 24 hours and 1 hour before the application of formaldehyde in doses of 6 and 18 mg/kg. The formaldehyde solution with a concentration of 30% was administered to the control group. Dexamethasone and diclofenac were used as reference agents. Dexamethasone (0.6 mg/kg) and diclofenac (8 mg/kg) were intragastrically administered 24 hours and 1 hour before the application of formaldehyde. The results of the study are presented in table 10.

It is obvious from table 10 that the administration of formaldehyde (the control) results in the significant increase in the concentration of the dye in the tissue, which indicates pharynx inflammation in rats—pharyngitis. The test compound has shown the significant protection against the pharyngitis caused by formaldehyde. Compound I had an effect in all tested doses (6 and 18 mg/kg)—the concentration of dye in the tissue has decreased 2.8 and 6.4 times, respectively, compared to the control. The administration of dexamethasone (0.6 mg/kg) also resulted in the decrease in the inflammation: the concentration of the dye has decreased 2.1 times. Diclofenac had no effect.

Thus, the obtained results have shown that Compound I has the pronounced anti-inflammatory effect in case of pharyngitis.

TABLE 10

Concentrations of the Evans blue dye in the pharynx tissue of rats

| Group | The concentration of the dye in the tissue, µg/mg |
|---|---|
| Intact | 0.029 ± 0.004 |
| Control (formaldehyde-30%) | 0.141 ± 0.015* |
| Compound I (6 mg/kg) | 0.051 ± 0.016*& |
| Compound I (18 mg/kg) | 0.022 ± 0.003& |
| Dexamethasone 0.6 mg/kg | 0.066 ± 0.009*& |
| Diclofenac 8 mg/kg | 0.112 ± 0.031* |

Notes:
1 - *distinctions are statistically significant as compared to intact ($p < 0.05$);
2 - &distinctions are statistically significant as compared to intact ($p < 0.05$).

The Study of the Activity of Compound II on a Model of Bleomycin-Induced Lung Injury The model of the bleomycin-induced lung injury was implemented by the standard method Am J Respir Cell Mol Biol. 2009 V. 41(1). P. 50-58]. A bleomycin solution was endotracheally administered to male Balb/c mice once (4 units/kg in a volume of 50 µl). Compound II was intragastrically administered to C57BL/6 mice, twice: 1 hour before the administration of bleomycin and 12 hours after the administration of bleomycin. The bronchoalveolar lavage was collected 24 h after the administration of bleomycin. In the lavage, the total quantity of leukocytes was assessed and the leukocyte formula was determined.

The results of the study have shown that the intragastric administration of Compound II reduces the inflow of inflammatory cells into the bronchoalveolar space (Table 11). This provides grounds to conclude that Compound II has an anti-inflammatory effect on the lung injury.

TABLE 11

The quantity of cellular elements in the bronchoalveolar lavage of mice on the model of bleomycin-induced acute lung injury (M ± m, n = 10)

| Groups | A dose of compound, mg/kg | The quantity of cellular elements in 1 μl of the bronchoalveolar lavag | | | | |
|---|---|---|---|---|---|---|
| | | Leukocytes | Neutropils | Eosinophils | Macrophages | Lymphocytes |
| Intact | — | 151.32 ± 23.85 | 8.51 ± 4.12 | 0.40 ± 0.30 | 122.15 ± 14.69 | 0.00 ± 0.00 |
| Control | — | 412.13 ± 65.00* | 212.39 ± 37.00* | 0.00 ± 0.00 | 199.74 ± 34.00 | 0.00 ± 0.00 |
| Compound II | 3 | 122.34 ± 15.96& | 82.77 ± 16.87*& | 0.00 ± 0.00 | 39.57 ± 7.91*& | 0.00 ± 0.00 |
| | 30 | 199.12 ± 46.59& | 55.21 ± 12.53*& | 0.00 ± 0.00 | 143.90 ± 39.26 | 0.00 ± 0.00 |

Notes:
*the distinction from the intact group according to Student's t-test at $p < 0.05$;
&the distinction from the control group according to Student's t-test at $p < 0.05$.

The Study of the Activity of Compound IV on a Rat Model of Lipopolysaccharide-Induced Acute Lung Injury The model of lipopolysaccharide-induced acute lung injury was implemented using the standard method [Lin Tong, Jing Bi, Xiaodan Zhu, Guifang Wang, Jie Liu, Linyi Rong, Qin Wang, Nuo Xu, Ming Zhong, Duming Zhu, Yuanlin Song, Chunxue Bai. Keratinocyte growth factor-2 is protective inlipopolysaccharide-induced acute lung injury in rats//Respiratory Physiology & Neurobiology. 2014. V. 201. P. 7-14]. A lipopolysaccharide (LPS) solution prepared with the saline solution was endotracheally administered to female Wistar rats. Animals of the false pathology group were injected with the saline solution in the same volume. The bronchoalveolar lavage (BAL) was collected from the animals 48 h after the administration of LPS. The BAL capture was performed under anesthesia by washing the lungs with 5 ml of saline solution heated up to 37° C. through the trachea using a syringe dispenser.

In the bronchoalveolar lavage fluid, the absolute count of cellular elements in 1 μl of the lavage was calculated using Goryaev's camera. Then, the bronchoalveolar lavage was centrifuged at 200 g for 10 minutes. Smears were prepared from the cell sediment, which smears were further fixed in methanol and stained by Romanovsky-Giemsa for counting endopulmonary cytogram.

Compound IV was intragastrically administered to rats twice, 1 hour before the administration of the LPS and 24 hours after the administration of the LPS).

The results of the study have shown that the intragastric administration of Compound IV reduces the influx of inflammatory cells into the bronchoalveolar space (Table 12). This provides grounds to conclude that Compound IV has the anti-inflammatory effect in case of lung injury.

TABLE 12

A quantity of cellular elements in the bronchoalveolar lavage of rats on the model of LPS--induced acute lung injury (Mm, n = 10)

| Groups | A dose of compound, mg/kg | A quantity of cellular elements in 1 μl of the bronchoalveolar lavage | | | | |
|---|---|---|---|---|---|---|
| | | Leukocytes | Neutrophils | Eosinophils | Macrophages | Lymphocytes |
| Intact | — | 2263 ± 311 | 199 ± 59 | 0 ± 0 | 2063 ± 265 | 0 ± 0 |
| False pathology | | 3434 ± 351 | 825 ± 115 | 0 ± 0 | 2609 ± 302 | 0 ± 0 |
| Control | — | 12937 ± 1837.5*# | 3304 ± 597*# | 0 ± 0 | 9633 ± 1502*# | 0 ± 0 |
| Compound IV | 1.8 | 4485 ± 815*& | 785 ± 181& | 0 ± 0 | 3699 ± 653& | 0 ± 0 |

Notes:
*the distinction from the intact group according to Kruskall-Wallis test at $p < 0.05$;
the distinction from the false pathology group according to Kruskall-Wallis test at $p < 0.05$;
&the distinction from the control group according to Kruskall-Wallis test at $p < 0.05$.

The study of the Activity of Compound II, Compound IV, Compound VI, Compound I on a Rat Model of Febrile Reaction The model of febrile reaction was implemented using the standard method [J Neurosci Methods.2005. V. 147. P. 29-35]. Wistar rats were subcutaneously injected with a 20% suspension of baker's yeast (12 ml/kg). Compounds I, II, IV, VI, VIII were intragastrically administered once, 14 hours after the administration of the yeast. The rectal temperature was measured by an electrothermometer before the administration of pyrogen and at the highest point of the thermal reaction development—19 hours after it. The antipyrogenic effect of the compounds was studied in 2-7 experiments.

The results of the study have shown that the intragastric administration of the studied compounds reduced the gain in the rectal temperature of the body of rats (Tables 13-17). The obtained data allow to conclude that Compounds I, II, IV, VI, VIII have the antipyrogenic effect.

TABLE 13

The gain in body rectal temperature 19 hours after the subcutaneous administration of yeast to rats, ° C. (M ± m, n = 30-90)

| Group | A dose of compound, mg/kg | A quantity of animals in the group | The gain in body rectal temperature, ° C. |
|---|---|---|---|
| Intact | — | 70 | 0.05 ± 0.05 |
| Control | — | 90 | 1.70 ± 0.06* |
| Compound II | 0.18 | 40 | 1.18 ± 0.08*& |
|  | 0.6 | 30 | 0.78 ± 0.07*& |
|  | 1.8 | 70 | 1.09 ± 0.06*& |

Notes:
*the distinction from the intact group according to Kruskall-Wallis test at $p < 0.05$;
&the distinction from the control group according to Kruskall-Wallis test at $p < 0.05$.

TABLE 14

The gain in body rectal temperature 19 hours after the subcutaneous administration of yeast to rats, ° C. (M ± m, n = 30-90)

| Group | A dose of compound, mg/kg | A quantity of animals in the group | The gain in body rectal temperature, ° C. |
|---|---|---|---|
| Intact | — | 70 | 0.30 ± 0.10 |
| Control | — | 90 | 1.90 ± 0.10* |
| Compound VI | 0.018 | 40 | 0.90 ± 0.10*& |
|  | 0.18 | 30 | 1.00 ± 0.20*& |

Notes:
*the distinction from the intact group according to Student's t-test at $p < 0.05$;
&the distinction from the control group according to Student's t-test at $p < 0.05$.

TABLE 15

The gain in body rectal temperature 19 hours after the subcutaneous administration of yeast to rats, ° C. (M ± m, n = 40-70)

| Group | A dose of compound, mg/kg | A quantity of animals in the group | The gain in body rectal temperature, ° C. |
|---|---|---|---|
| Intact | — | 50 | 0.01 ± 0.08 |
| Control | — | 70 | 1.70 ± 0.07* |
| Compound I | 0.018 | 40 | 1.01 ± 0.09*& |
|  | 0.06 | 40 | 0.88 ± 0.11*& |
|  | 0.18 | 50 | 1.01 ± 0.08*& |
|  | 0.6 | 40 | 0.88 ± 0.11*& |
|  | 1.8 | 50 | 1.14 ± 0.09*& |

Notes:
*the distinction from the intact group according to Kruskall-Wallis test at $p < 0.05$;
&the distinction from the control group according to Kruskall-Wallis test at $p < 0.05$.

TABLE 16

The gain in body rectal temperature 19 hours after the subcutaneous administration of yeast to rats, ° C. (M ± m n = 40-70)

| Group | A dose of compound, mg/kg | A quantity of animals in the group | The gain in body rectal temperature, ° C. |
|---|---|---|---|
| Intact | — | 50 | 0.03 ± 0.07 |
| Control | — | 70 | 1.75 ± 0.07* |
| Compound IV | 0.018 | 40 | 1.18 ± 0.08*& |
|  | 0.06 | 40 | 1.28 ± 0.07*& |
|  | 0.18 | 50 | 1.36 ± 0.05* |
|  | 0.6 | 40 | 1.27 ± 0.09*& |

Notes:
*the distinction from the intact group according to Kruskall-Wallis test at $p < 0.05$;
&the distinction from the control group according to Kruskall-Wallis test at $p < 0.05$.

TABLE 17

The gain in body rectal temperature 19 hours after the subcutaneous administration of yeast to rats, ° C. (M ± m, n = 40-70)

| Group | A dose of compound, mg/kg | A quantity of animals in the group | The gain in body rectal temperature, ° C. |
|---|---|---|---|
| Intact | — | 10 | 0.32 ± 0.21 |
| Control | — | 10 | 1.83 ± 0.11* |
| Compound VIII | 1.8 | 10 | 1.16 ± 0.12*& |

Notes:
*the distinction from the intact group according to Kruskall-Wallis test at $p < 0.05$;
&the distinction from the control group according to Kruskall-Wallis test at $p < 0.05$.

The Study of the Activity of Compound I and Compound IV on a Model of a Specific Pain Reaction by the Method of Chemical Irritation of the Peritoneum ("Abdominal Constriction" Test)

The model of the specific pain reaction by the method of chemical stimulation of peritoneum ("abdominal constriction" test) was carried out according to the standard procedure. To conduct the "abdominal constriction" test, Balb/c mice were intraperitoneally administered with 1% acetic acid in a volume of 10 ml per kg of the animal body weight. Compounds I, IV, VII, IX, X were intragastrically administered, once, 1 hour before the administration of acetic acid. A quantity of constrictions (convulsive twitching of the abdominal muscles accompanied with stretching hind quarters and arching) was evaluated 15 minutes after the administration of acetic acid.

The results of the study have shown that the intragastric administration of Compounds I, IV, VII, IX, X significantly reduces the quantity of constrictions in mice, caused by the intraperitoneal administration of acetic acid (Tables 18-19). The obtained results allow to conclude that Compounds I, IV, VII, IX, X has the pronounced therapeutic effect in case of pain syndrome.

TABLE 18

The quantity of acetic constrictions on the model of the specific pain reaction by the method of chemical stimulation of peritoneum ("abdominal constrictions" test) (M ± m, n = 10-31)

| Group | A dose of compound, mg/kg | A quantity of animals in the group | Quantity of constrictions for 15 minutes |
|---|---|---|---|
| Control | — | 31 | 34.68 ± 2.40 |
| Compound I | 0.03 | 10 | 22.70 ± 2.14* |
|  | 0.3 | 20 | 13.90 ± 2.23* |
|  | 3 | 20 | 18.65 ± 2.44* |
|  | 30 | 20 | 21.15 ± 2.97* |
| Compound IV | 0.03 | 10 | 23.60 ± 2.54* |
|  | 0.3 | 10 | 15.50 ± 2.63* |
|  | 3 | 10 | 19.20 ± 3.43* |
|  | 30 | 10 | 15.30 ± 3.10* |
| Ketorol | 15 | 20 | 23.60 ± 1.87* |

Notes:
&the distinction from the control group according to Student's t-test at $p < 0.05$.

TABLE 19

The quantity of acetic constrictions on the model of the specific pain reaction by the method of chemical stimulation of peritoneum ("abdominal constrictions" test) (M ± m, n = 10-31)

| Group | A dose of compound, mg/kg | A quantity of animals in the group | Quantity of constrictions for 15 minutes |
|---|---|---|---|
| Control |  | 10 | 48 ± 5.71 |
| Compound VII | 0.3 | 10 | 17.6 ± 2.81* |
| Compound IX | 0.3 | 10 | 11.6 ± 3.5* |
| Compound X | 0.3 | 10 | 17.2 ± 3.4* |

Notes:
&the distinction from the control group according to Student's t-test at $p < 0.05$.

Study of the Activity of Compound 1 on the Model of Thermal Pain Irritation "Hot Plate"

The model of thermal pain irritation "hot plate" was carried out according to the standard procedure [Barrot M. Tests and models of nociception and pain in rodents. Neuroscience. 2012 Jun. 1; 211:39-50.]. Compound I and Compound II were intragastrically administered to Balb/c mice once. After 1 hour after the administration of the preparation, the "hot plate" test was carried out. To conduct the "hot plate" test, the mice were placed on the hot plate, the temperature (+55±1° C.) of which is constant.

The time of first manifestations of the pain response in mice (paw licking, jumping) was registered and the mean latent time of the threshold of pain sensitivity (TPS, sec) in each group was calculated.

The results of the study have shown that the intragastric administration of compound under study by 1.5 times has increased the threshold of pain sensitivity of mice in the "hot plate" test. The pharmacological effect of Compound 1 lasted for at least 24 hours (Table 12). The obtained data allow to conclude that Compound I and Compound II have the pronounced analgesic effect in case of pain syndrome.

TABLE 20

The threshold of pain sensitivity (TPS) on the model of thermal pain irritation "hot plate", % to the values before the administration of the preparation (M ± m, n = 20)

| Group | A dose of compound, mg/kg | After 1 hour, % to the background |
|---|---|---|
| Control |  | 72.51 ± 5.80 |
| Compound I | 0.3 | 101.13 ± 9.64* |
|  | 3 | 95.28 ± 6.79* |
|  | 30 | 104.55 ± 8.52* |

TABLE 20-continued

The threshold of pain sensitivity (TPS) on the model of thermal pain irritation "hot plate", % to the values before the administration of the preparation (M ± m, n = 20)

| Group | A dose of compound, mg/kg | After 1 hour, % to the background |
|---|---|---|
| Compound II | 0.3 | 97.43 ± 6.43* |
|  | 3 | 90.54 ± 6.59* |
|  | 30 | 110.18 ± 11.9* |

Notes:
&the distinction from the control group according to Student's t-test at $p < 0.05$.

The Study of the Activity of Compound II on the Model of Spontaneous Obesity in db/db Mice To model the spontaneous obesity, db/db mice that carry the leptin receptor-Leprdb- (db) recessive gene ($8^{th}$ linkage group, $4^{th}$ chromosome) were used [Cardiovasc. Diabetol. 2012. V. 11. P. 139-147; Biochem. Biophys. Res. Commun. 2016. V. 472. P. 603-609].

Compound II was administered intragastrically, starting from the $7^{th}$ week of the life of animals. Weekly, on 6-12 weeks of life, the animals were measured for their body weight.

The results of the study have shown that on the obesity model the intragastric administration of Compound II in a dose of 7.5 mg/kg to mice reduces the weight gain of db/db mice (Table 21).

The obtained results suggest the therapeutic effect of Compound II in case of obesity. The therapeutic effect begins as early as 4 weeks of using Compound II.

The Study of the Activity of Compound II on the Model of Metabolic Syndrome

The metabolic syndrome model was implemented by keeping male Wistar rats for 16 weeks on a high-fat diet ("cafeteria diet") in accordance with the standard method [Rothwell N. J., Stock M. J., Warwick B. P. Energy balance and brown fat activity in rats fed cafeteria diets or high-fat, semisynthetic diets at several levels of intake//Metabolism. 1985. Vol. 34(5). P. 474-480].

From the $10^{th}$ to the $16^{th}$ week of the diet, Compound II was intragastrically administered once a day to animals of the experimental groups. The evaluation of the activity of the test compound was performed using weekly measurement of body weight.

The results of the study have shown that the intragastric administration of Compound II reduces the weight gain of animals. The pharmacological effect begins to appear from the $5^{th}$ week of therapy (Table 22).

Thus, on on the metabolic syndrome model Compound II reduces the obesity in animals.

TABLE 21

The gain of body weight of animals relative to the beginning of the administration of Compound II on the model of spontaneous obesity in db/db mice (M ± m)

| | | The age of the animals at the time of taking indices, weeks | | | | | | |
|---|---|---|---|---|---|---|---|---|
| | A dose of compound, | 6 | 7 | 8 | 9 | 10 | 11 | 12 |
| | | Weeks of the administration of Compound I | | | | | | |
| Groups | mg/kg | 0 | 1 | 2 | 3 | 4 | 5 | 6 |
| Intact (db/m) | | 100.0 ± 4.4 | 100.0 ± 0.9 | 103.3 ± 0.9 | 106.0 ± 0.9 | 109.8 ± 1.5 | 113.3 ± 1.1 | 116.5 ± 1.5 |
| Control (db/db) | | 100.0 ± 2.9 | 109.6 ± 3.1* | 118.3 ± 3.3* | 126.2 ± 3.3* | 131.0 ± 3.4* | 134.2 ± 4.2* | 139.2 ± 4.8* |

TABLE 21-continued

The gain of body weight of animals relative to the beginning of the administration of Compound II on the model of spontaneous obesity in db/db mice (M ± m)

| | A dose of compound, | The age of the animals at the time of taking indices, weeks | | | | | | |
|---|---|---|---|---|---|---|---|---|
| | | 6 | 7 | 8 | 9 | 10 | 11 | 12 |
| | | Weeks of the administration of Compound I | | | | | | |
| Groups | mg/kg | 0 | 1 | 2 | 3 | 4 | 5 | 6 |
| Compound II | 0.75 | 100.0 ± 1.7 | 108.5 ± 1.5* | 119.6 ± 3.7* | 123.9 ± 3.8* | 126.5 ± 4.0* | 127.3 ± 4.2* | 129.8 ± 5.2* |
| | 7.5 | 100.0 ± 2.3 | 111.4 ± 2.9* | 119.9 ± 2.6* | 122.1 ± 2.5* | 121.7 ± 2.5*& | 121.7 ± 3.1*& | 109.4 ± 4& |

Notes:
*the distinction from the intact group according to Student's t-test at $p < 0.05$;
&the distinction from the control group according to Student's t-test at $p < 0.05$.

TABLE 22

A body weight of rats on the model of metabolic syndrome (M ± m, n = 12)

| Weeks of the study | Weeks of the therapy | Intact | Control | Compound II (1.5 mg/kg) |
|---|---|---|---|---|
| 0 | — | 245.50 ± 5.30 | 250.17 ± 3.95 | 239.67 ± 3.27 |
| 1 | — | 259.08 ± 5.80 | 312.83 ± 8.84*# | 292.08 ± 4.70*# |
| 2 | — | 276.42 ± 6.20# | 325.33 ± 7.60*# | 307.33 ± 5.53*# |
| 3 | — | 305.00 ± 7.30# | 345.08 ± 9.84*# | 327.25 ± 7.81*# |
| 4 | — | 327.92 ± 6.50# | 374.75 ± 11.28*# | 355.50 ± 9.05*# |
| 5 | — | 348.00 ± 5.70# | 409.25 ± 12.37*# | 379.42 ± 7.41*# |
| 6 | — | 354.83 ± 5.60# | 471.33 ± 12.88*# | 443.00 ± 7.70*# |
| 7 | — | 321.00 ± 5.60# | 498.25 ± 13.08*# | 469.08 ± 6.38*# |
| 8 | — | 341.08 ± 5.60# | 520.83 ± 13.77*# | 491.83 ± 6.04*# |
| 9 | — | 359.17 ± 6.00# | 546.50 ± 14.78*# | 518.25 ± 6.04*# |
| 10 | 1 | 374.17 ± 6.60# | 559.08 ± 16.87*# | 528.08 ± 6.01*# |
| 11 | 2 | 394.75 ± 6.80# | 571.92 ± 18.62*# | 547.92 ± 8.27*# |
| 12 | 3 | 393.33 ± 7.90# | 579.50 ± 18.66*# | 551.00 ± 8.36*# |
| 13 | 4 | 394.17 ± 8.50# | 592.58 ± 18.47*# | 553.58 ± 8.52*# |
| 14 | 5 | 396.83 ± 10.20# | 613.17 ± 18.86*# | 563.67 ± 9.75*&# |
| 15 | 6 | 398.42 ± 9.50# | 631.50 ± 18.94*# | 570.75 ± 9.13*&# |
| 16 | 7 | 397.42 ± 8.30# | 627.17 ± 18.72*# | 572.08 ± 8.23*&# |

Notes:
*the distinction from the intact group according to Student's t-test at $p < 0.05$;
&the distinction from the control group according to Student's t-test at $p < 0.05$;
the distinction from values at 0 week of the study according to the Student's t-test at $p < 0.05$.

The Study of the Activity of Compound I and Compound II on a Mouse Model of Psoriasis The induction of psoriasis in mice was carried out according to standard method [European Journal of Pharmacology. 2015. V. 756. P. 43-51]. Aldar cream (5% imiquimod) was applied to female Balb/c mice on the inner side of the right ear, 1 time per day for 7 days (0-6$^{th}$ day) in an amount of 30 mg/mouse. Vaseline was applied to intact animals. Compound I, Compound II and the reference drug (cyclosporin) were intragastrically administered to the animals, daily, 1 time per day for 6 days (0-5$^{th}$ day). Euthanasia was performed 24 hours (6$^{th}$ day) after the last application of Aldara cream. Daily on the 0, 2, 3, 4, 5$^{th}$ day in the morning, before the next application of Aldar cream and before euthanasia, the thickness of the right ear was measured.

The assessment of the severity of psoriasis was carried out by measuring the gain in the thickness of the affected ear over time.

The results of the study are presented in table 23.

TABLE 23

The gain of the thickness of the affected ear at particular day of the study to day 0 on the mouse model of psoriasis, % (M ± m, n = 10)

| Group | A dose of compound, mg/kg | The gain of the thickness of the affected ear at particular day of the study to day 0, % | | | |
|---|---|---|---|---|---|
| | | Day 3 | Day 4 | Day 5 | Day 6 |
| Intact | — | 4.86 ± 0.9 | 7.8 ± 0.98 | 9.81 ± 1.83 | 14.8 ± 1.3 |
| Control | — | 40.3 ± 5.3* | 67.7 ± 7.9* | 82.6 ± 9.5* | 101 ± 9.8* |
| Compound I | 0.3 | 38.3 ± 5.8* | 45.2 ± 4.1*& | 57.3 ± 3.9*& | 62.8 ± 5.4*& |

TABLE 23-continued

The gain of the thickness of the affected ear at particular day of the study to day 0 on the mouse model of psoriasis, % (M ± m, n = 10)

| Group | A dose of compound, mg/kg | The gain of the thickness of the affected ear at particular day of the study to day 0, % | | | |
|---|---|---|---|---|---|
| | | Day 3 | Day 4 | Day 5 | Day 6 |
| Compound II | 0.3 | 35.3 ± 2.1* | 48.1 ± 2.8*& | 59.6 ± 4.5*& | 70.6 ± 4.4*& |

Notes:
*the distinction from the intact group according to Student's t-test at p < 0.05;
&the distinction from the control group according to Student's t-test at p < 0.05.

The results of the study have shown that the intragastric administration of Compound I and Compound II on ther mouse model of psoriasis reduces the gain of the thickness of the affected ear of animals. This demonstrates the therapeutic effect of Compounds I and II in case of psoriasis.

Thus, on the mouse model of psoriasis, Compounds I and II have the pronounced therapeutic effect.

The Study of the Activity of Compound I and Compound II on a Mouse Model of Atopic Dermatitis The model of atopic dermatitis was implemented by the standard method [J Ginseng Res. 2011. Vol. 4.—P. 479-86]. Atopic dermatitis was modeled on male balb/c mice. 1-Chloro-2,4-dinitrobenzene (DNHB) was used as an inducer of contact dermatitis. On days 0 and 12 of the experiment, 100 μl of a 2% solution of DNHB was applied to pre-shaved back areas of animals to sensitize the body. On the $17^{th}$ day, 20 μl of the 2% alcoholic solution of DNHB was applied to the right "experimental" ear twice with an interval of 1 hour. Ethanol was applied to intact animals, instead of the DNHB solution. Animals in the false immunization group were sensitized with ethanol. Compound I and Compound II were intragastrically administered once a day from $8^{th}$ to $17^{th}$ day. On day 18, the animals were slaughtered. To assess the degree of edema after euthanasia, the mass of the "experimental" and "control" ears was determined. The reaction index (RI) expressed as a percentage of the difference between the masses of the "experimental" and "control" ears was calculated.

The results of the study are presented in table 24.

TABLE 24

The difference between the mass of the "experiment" and "control" ear in mices and the reaction index on the mouse model of atopic dermatitis (M ± m, n = 12)

| Name of the group | The difference between the mass of the "experiment" and "control" ear (mg) | Reaction index (%) |
|---|---|---|
| Intact | −0.001 ± 0.002 | −0.82 ± 5.3 |
| False immunization | 0.018 ± 0.003* | 57.8 ± 11.3* |
| Control of pathology | 0.029 ± 0.002*# | 83.3 ± 6.1* |
| Compound I (3 mg/kg) | 0.007 ± 0.003#& | 25.4 ± 10.2*#& |
| Compound II (3 mg/kg) | 0.013 ± 0.002*& | 38.1 ± 7.7*& |

Notes:
*the distinction from the intact group according to Student's t-test at p < 0.05;
the distinction from the flase immunization group according to Student's t-test at p < 0.05;
&the distinction from the control group according to Student's t-test at p < 0.05.

The results of the study have shown that the intragastric administration of Compound I and Compound II on the mouse model of atopic dermatitis reduces the reaction index of the pathological process. This demonstrates the therapeutic effect of Compounds I and II on atopic dermatitis.

Thus, on the mouse model of atopic dermatitis model Compounds I and II have the pronounced therapeutic effect.

Study of the Effect of Compound II on Macrophase Chemotaxis In Vivo in a Carrageenan Air Pouch To assess the effectiveness of the drug on the activity of cells of the immune system at the preclinical stage of research, as a rule, various models of the acute inflammatory process are used. Today, the most frequently used models are those in which the pathological process develops in a confined cavity. These models make it possible to quite closely simulate diseases in which the aberrant activity of cells of the immune system is localized in the specific cavity (peritonitis, cholangitis, arthritis) (J Pharmacol Toxicol Methods. 1994 November; 32(3):139-47). The carrageenan air pouch model is often used at the preclinical stage of research to study the pathological processes associated with the aberrant activity of cells of the immune system, localized in the isolated cavity. In this model, the isolated pouch is formed by a subcutaneous injection of air into the intracapsular region of the back of a mouse or rat. The subcutaneous injection of air into the back area results in morphological changes in the cellular lining of the pouch for several days. The pouch consists mainly of macrophages and fibroblasts and is well vascularized. On the sixth day from the moment of the formation of the air pouch, a λ-carrageenan solution is administered into the cavity of the air pouch. Carragenan interacts with TLR4 receptors on the surface of macrophages lining the intracapsular region of the pouch, which causes their activation and the subsequent synthesis of chemokines and other mediators (IL-1; IL-6; TNFα, IL-8, prostaglandins and leukotrienes, NO) and also the migration of cells of the immune system inside the pouch.

The study of the activity of Compound II was performed on male Balb/c mice according to the standard method (Curr Protoc Pharmacol. 2012 March; Chapter 5: Unit 5.6). Compound II was administered intragastrically to the experimental groups at a dose of 3 mg/kg immediately before the administration of carrageenan and then every 10-12 hours. The last administration was 12 hours before the slaughter.

Euthanasia by the inhalation of $CO_2$ was performed in respect to individual groups of animals 48 hours after the injection of λ-carrageenan. Immediately after the euthanasia, 1 ml of saline solution containing 5.4 mM of EDTA of room temperature was introduced into the pouch with a sterile syringe 25 G. After gentle massage of the region of the air pouch, a sagittal incision was made across the pouch and exudate was collected by a dispenser into sterile vials having a volume of 15 ml. In the exudate, the absolute count of cellular elements per 1 µl of the lavage (cytosis) was determined using Goryaev's chamber. Then the exudate was centrifugated at 200 g for 10 minutes. Smears were prepared from the cell pellet, which smears were subsequently fixed in methanol (5 min) and stained according to Romanovsky-Giemsa (40 min at t 20-22° C.). On smears routinely using a microscope Olympus bx51 (magnification 100) the number of macrophages was counted. The cell calculation was made up to 100 pcs.

The carried out studies have shown that the use of Compound II reduced the influx of leukocytes and macrophages 10 times (to the level of intact control) (Table 25). Thus, Compound II may have the potential to treat a wide range of diseases, such as Crohn's disease, ulcerative colitis, peritonitises, and arthritises.

TABLE 25

A cell number of the immune system in the excudate from the carraggenan pouch under the study fo the activity of Compound II on the model of macrophage chemotaxis (carrageenan air pouch), × $10^9/1$ (M ± m, n = 10)

| Groups | A quantity of cellular elements in 1 µl of the excudate, × $10^9/1$ | |
|---|---|---|
| | Leukocytes | Macrophages |
| Intact | 0.9 ± 0.2 | 0.6 ± 0.1 |
| Control | 9.9 ± 1.5* | 7.7 ± 1.5* |
| Compound II (3 mg/kg) | 1.0 ± 0.1 & | 0.5 ± 0.1 & |

*distinctions which are statistically significant compared to the intact group ($p < 0.05$);
& distinctions statistically significant compared to the control group ($p < 0.05$).

The Study of the Effect of Compound II on Macrophase Chemotaxis In Vivo on a Model of Thioglycolate Peritonitis The study was performed on male balb/c mice using the standard method (J Leukoc Biol. 2009 August; 86(2):361-70). Mice of the control group were intraperitoneally administered with 2 ml of 3% thioglycolic medium stored for 1 month. Intact animals were intraperitoneally infused with 2 ml of saline solution. Compounds II was intragastrically administered to experimental groups of animals 1 hour before the administration of thioglycolate, 24 and 48 hours after the administration of thioglycolate in a dose of 1 mg/kg. After 72 hours, the animals were euthanized in a $CO_2$ chamber, the peritoneum area was moistened with 70% alcohol, the skin was carefully cut off on the abdominal cavity, and 5 ml of cold phosphate-saline buffer containing 0.1% EDTA was intraperitoneally injected with a syringe. After gentle massage of the abdominal cavity, the exudate was collected with a syringe into test tubes, the volume of the collected exudate was determined.

In the exudate, the absolute count of cellular elements per 1 µl of the lavage (cytosis) was determined using a Goryaev's chamber. Then the exudate was centrifuged at 200 g for 10 minutes. Smears were prepared from the cell pellet, which smears were subsequently fixed in methanol (5 min) and stained according to Romanovsky-Giemsa (40 min at t 20-22° C.). On smears routinely, using a microscope Olympus bx51 (magnification 10), the quantity of monocytes/macrophages was counted. The cell calculation was made up to 100 pcs.

The carried out studies have shown that the use of Compound II reduced the influx of macrophages into the peritoneal cavity of rats, induced by 3% thioglycolic medium, and reduces the severity of pathology induced by the administration of thioglycolic medium (Table 26). Thus, Compound II may have the potential to treat peritonitis's, Crohn's disease, and ulcerative colitis.

TABLE 26

A cell number of the immune system in the exudate from the abdominal cavity at the study of the activity of Compound II on the model of macrophage chemotaxis (thioglycolate peritonitis), × $10^9/1$ (M ± m, n = 10)

| Groups | A quantity of cellular elements in 1 µl of the exudate, × $10^9/1$ | |
|---|---|---|
| | Leukocytes | Monocytes |
| Intact | 0.71 ± 0.09 | 0.61 ± 0.07 |
| Control | 3.99 ± 0.42* | 3.66 ± 0.44* |
| Compound II (1 mg/kg) | 1.97 ± 0.36*& | 0.65 ± 0.12& |

*distinctions which are statistically significant compared to the intact group (p < 0.05);
&distinctions statistically significant compared to the control group (p < 0.05).

Investigation of the Activity of Compound II and Compound I on a Model of Adjuvant Arthritis Induced by the Administration of Freund's Complete Adjuvant The model of adjuvant arthritis was implemented on outbred male rats according to the standard method [Chem Pharm Bull (Tokyo). 2018. V. 66(4). P. 410-415]. On 0 and $5^{th}$ day, the Freund's complete adjuvant (Freund's Adjuvant, Complete (Pierce)) was subplantarly administered to animals in the right hind limb in a volume of 100 µl per animal. The volume of the right hind paw (affected) and the left hind paw (contralateral) was measured on 0, $14^{th}$, $16^{th}$, $18^{th}$, $21^{st}$, $25^{th}$, $28^{th}$ and $30^{th}$ day using a plethysmometer (Ugo Basel).

We estimated the primary (inflammatory) reaction by changing the volume of the affected paw, and estimated the secondary (immune) reaction by changing the volume of the contralateral paw. Compound II was intragastrically administered, daily, once a day, from the $14^{th}$ to the $30^{th}$ day of the study.

Results of the study are presented in tables 27-28.

The carried out study has shown that the use of administered Compound II reduces the gain of the volume of both the affected paw and contralateral paw. This allows to conclude that Compound II has both the anti-inflammatory effect and the immunotropic effect. Thus, Compound II has the high therapeutic potential to treat rheumatoid arthritis and other kinds of arthritis, and also arthroses.

TABLE 27

The gain of the volume of the affected paw on the model of adjuvant arthritis induced by the administration of the Freund's complete adjuvant, % (M ± m, n = 10)

| Group | A dose of compound, mg/kg | The gain of the volume of the affected paw, % to the initial level | | | | | | |
|---|---|---|---|---|---|---|---|---|
| | | Day 14 | Day 16 | Day 18 | Day 21 | Day 25 | Day 28 | Day 30 |
| Intact | | 1.8 ± 0.8 | 1.9 ± 0.7 | 1.4 ± 0.3 | 1.9 ± 0.4 | 2.2 ± 0.2 | 2.7 ± 0.2 | 3 ± 0.2 |
| Control | | 122.3 ± 6.4* | 118.7 ± 5.6* | 114.3 ± 2.1* | 98.9 ± 3.2* | 100.6 ± 2.6* | 102.5 ± 1.8* | 101.4 ± 2.8* |
| Compound II | 0.5 | 118.8 ± 3.6* | 105 ± 3.2* | 104.4 ± 2.7*& | 86.3 ± 3.9*& | 88.5 ± 2.4*& | 86.9 ± 2.3*& | 83.2 ± 2.2*& |

Notes:
*the distinction from the intact group according to Student's t-test at p < 0.05;
&the distinction from the control group according to Student's t-test at p < 0.05.

TABLE 28

The gain of the volume of the contralateral paw on the model of adjuvant arthritis induced by the administration of the Freund's complete adjuvant, % (M ± m, n = 10)

| Group | A dose of compound, mg/kg | The gain of the volume of the contralateral paw, % to the initial level | | | | | | |
|---|---|---|---|---|---|---|---|---|
| | | Day 14 | Day 16 | Day 18 | Day 21 | Day 25 | Day 28 | Day 30 |
| Intact | | 1.27 ± 0.3 | 1.59 ± 0.48 | 1.77 ± 0.25 | 1.62 ± 0.31 | 2.18 ± 0.3 | 2.76 ± 0.16 | 2.98 ± 0.3 |
| Control | | 5.48 ± 0.58* | 7.08 ± 1.24* | 21.69 ± 1.28* | 25.29 ± 1.69* | 20.16 ± 1.66* | 18.75 ± 1.13* | 17.51 ± 1.59* |
| Compound II | 0.5 | 5.39 ± 1.67* | 6.75 ± 1.58* | 18.48 ± 1* | 19.77 ± 1.67*& | 15.45 ± 1.21*& | 14.04 ± 1.75*& | 13.02 ± 0.94*& |

Notes:
*the distinction from the intact group according to Student's t-test at p < 0.05;
&the distinction from the control group according to Student's t-test at p < 0.05.

The Study of the Activity of Compound II on the Model of Carrageenan Edema

To assess the effect of Compound II on the functional status of the immune system, a model of the carrageenan-induced rat paw edema was used. Experiments were performed on male white nonlinear rats weighing 250-270 g. The acute paw inflammation in rats was caused by intraplantar administration (subcutaneously) of 1.5% solution of carrageenan in a volume of 0.1 ml into the right paw. The studied compound was intragastrically administered 1 hour before the administration of carrageenan. The effect of Compound II and the control substance (diclofenac) was assessed by the degree of reduction of paw edema in comparison with the intact left paw. The paw volume was assessed before the administration of Compound II and 2 hours after the administration of carrageenan.

Results of the study are presented in table 29.

TABLE 29

The effect of Compound II to inhibit the growth of rat paw edema (relative to control) in a model of the carrageenan-induced edema.

| Group | Induction of pathology | The administration of preparations | Lead time of the assessment | Inhibition of edema growth, % |
|---|---|---|---|---|
| Intact | | | 2 hours after the administration of carrageenan | 0 |
| Control | The intraplantar administration of 1.5% solution of carrageenan in a volume of 0.1 ml to the right paw | Intragastrically, once, 1 hour before the administration of carrageenan | | 0 |
| Compound II (1.8 mg/kg) | | | | 34 |
| Compound II (0.18 mg/kg) | | | | 34 |
| diclofenac sodium (8 mg/kg) | | | | 42 |

It is clear from the presented results that Compound II has the direct inhibitory effect on the growth of the paw edema and can be used to treat a wide range of diseases associated with the activity of cells of the immune system.

Study of the Activity of Compound II in a Rat Model of Diabetic Nephropathy

The rat model of diabetic nephropathy was induced by the prolonged keeping of animals on the intake of a high-fat diet and single or double intraperitoneal administration of streptozotocin in a dose of 30 mg/kg (Int J Clin Exp Med. 2015 Apr. 15; 8(4):6388-96).

The animals were kept on the high-fat diet for 16 weeks; on the $9^{th}$ week, streptozotocin was administered intraperitoneally twice (2 consecutive days) in a dose of 30 mg/kg. 7 days after the administration of streptozotocin, the administration of Compound II was started. The substance was administered daily intragastrically once a day in a dose of 50 mg/kg.

The intragastric administration of Compound II beginning from the $10^{th}$ week of the study has reduced the daily protein content in the urine of experimental animals to the level of intact control (Table 30). The results allow to conclude that Compound II has the therapeutic effect in case of diabetic nephropathy.

TABLE 30

The biochemical analysis of urine after 6 weeks of the intragastric administration of Compound II to rats in a model of diabetic nephropathy induced by a high-fat diet and the administration of streptozotocin (15 weeks of the high-fat diet).

| Groups | A dose and regimen of the administration of streptozotocin | A quantity of animals | Dieresis, ml/18 h. | Daily protein, µg/18 h | ACR (protein(µg/l)/ creatinine (mg/l) |
|---|---|---|---|---|---|
| Intact | — | 8 | 4.35 ± 0.5 | 1041.2 ± 153.5 | 273.2 ± 68.0 |
| Control | 30 mg/kg, doubly | 14 | 8.32 ± 1.5 | 3718.2 ± 572.7* | 952.8 ± 186.4* |

TABLE 30-continued

The biochemical analysis of urine after 6 weeks of the intragastric administration of Compound II to rats in a model of diabetic nephropathy induced by a high-fat diet and the administration of streptozotocin (15 weeks of the high-fat diet).

| Groups | A dose and regimen of the administration of streptozotocin | A quantity of animals | Dieresis, ml/18 h. | Daily protein, μg/18 h | ACR (protein(μg/l)/ creatinine (mg/l) |
|---|---|---|---|---|---|
| Compound II (5 mg/kg) | 30 mg/kg, doubly | 12 | 7.45 ± 1.0 | 1846.3 ± 337.6* & | 202.3 ± 26.8 & |

*distinctions which are statistically significant compared to the intact group (p < 0.05);
& distinctions statistically significant compared to the control group (p < 0.05).

Although the invention has been described with a reference to the disclosed embodiments, it should be obvious to those skilled in the art that the specific experiments described in detail are given only to illustrate the present invention and should not be considered as limiting the scope of the invention in any way. It should be clear that it is possible to implement various modifications without the departure from the essence of the present invention.

The invention claimed is:

1. A method for treatment of a disorder comprising administering to a subject in need of treatment a therapeutically effective amount of a compound, wherein the compound is

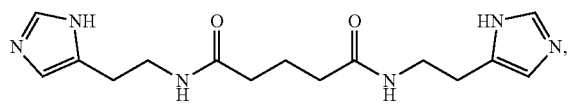

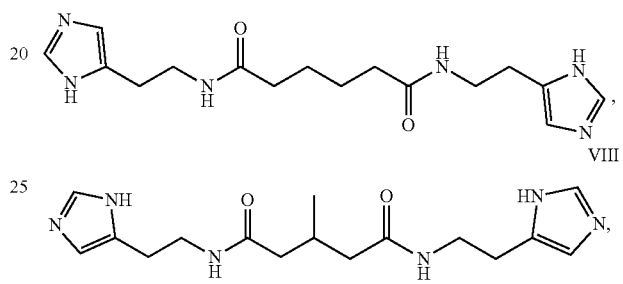

-continued

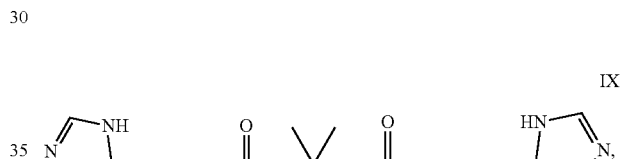

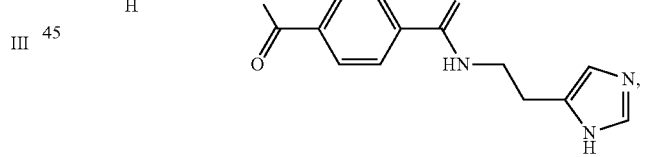

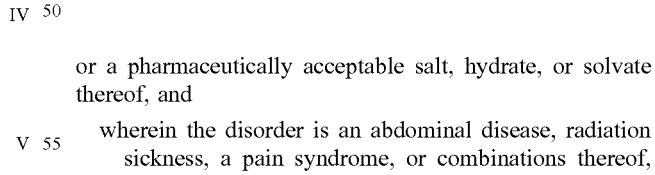

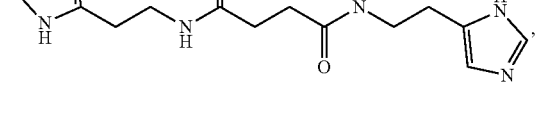

or a pharmaceutically acceptable salt, hydrate, or solvate thereof, and wherein the disorder is an abdominal disease, radiation sickness, a pain syndrome, or combinations thereof, fever, atopic dermatitis, psoriasis, Crohn's disease, obesity, or non-alcohol fatty liver disease.

2. The method of claim 1, wherein the abdominal disease is peritonitis.

3. The method of claim 1, wherein the abdominal disease is ulcerative colitis.

4. A method for treatment of a lung disease, a respiratory tract disease, or both comprising administering to a subject in need of treatment a therapeutically effective amount of a compound, wherein the compound is

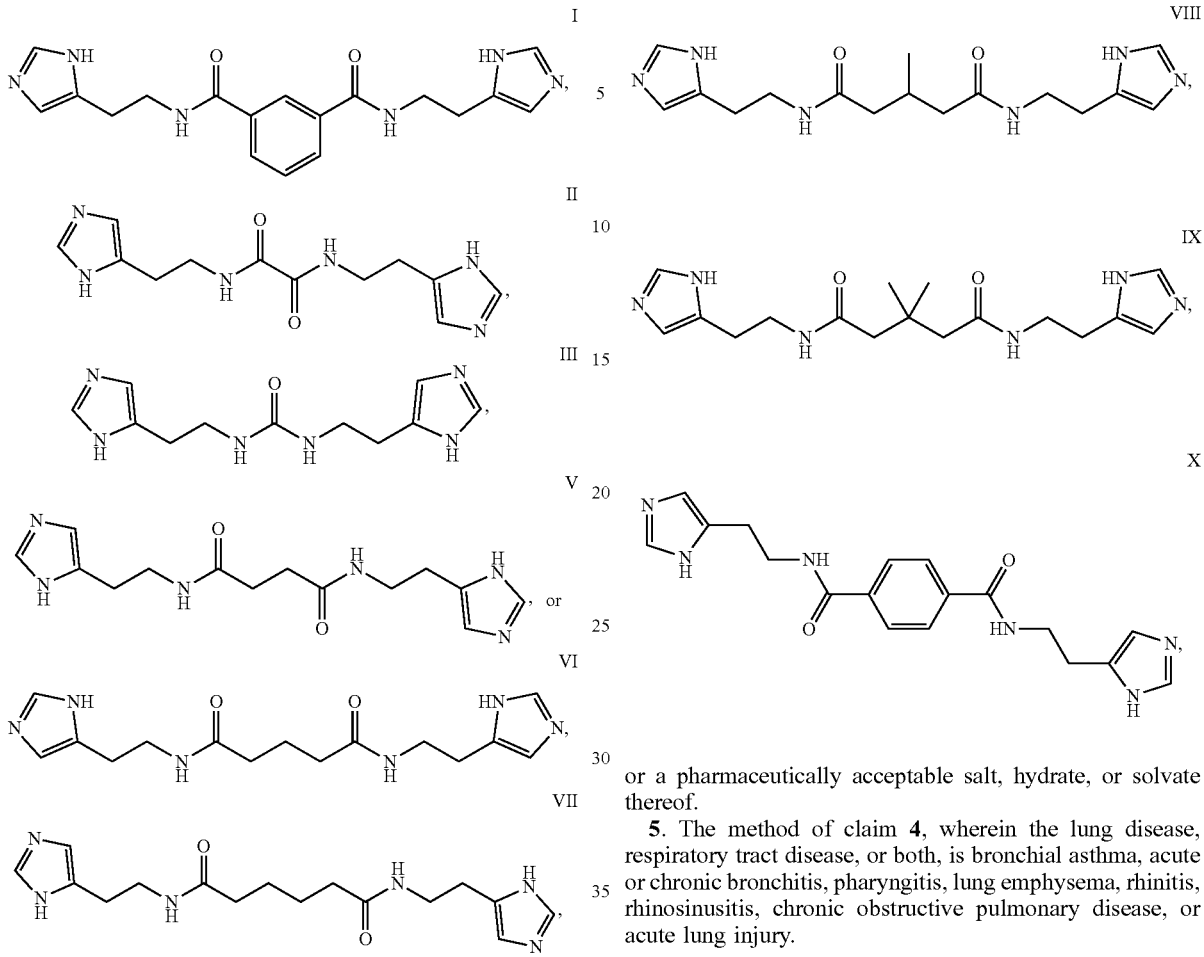
or a pharmaceutically acceptable salt, hydrate, or solvate thereof.
5. The method of claim 4, wherein the lung disease, respiratory tract disease, or both, is bronchial asthma, acute or chronic bronchitis, pharyngitis, lung emphysema, rhinitis, rhinosinusitis, chronic obstructive pulmonary disease, or acute lung injury.
* * * * *